United States Patent
Wang et al.

(10) Patent No.: US 8,586,348 B2
(45) Date of Patent: Nov. 19, 2013

(54) LATERAL FLOW MICROFLUIDIC ASSAYING DEVICE AND RELATED METHOD

(75) Inventors: Jun Wang, Pasadena, CA (US); James R. Heath, South Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 0 days.

(21) Appl. No.: 13/240,347

(22) Filed: Sep. 22, 2011

(65) Prior Publication Data

US 2012/0070833 A1    Mar. 22, 2012

Related U.S. Application Data

(60) Provisional application No. 61/385,432, filed on Sep. 22, 2010.

(51) Int. Cl.
*C12M 1/00* (2006.01)
*C12M 1/34* (2006.01)
*C12Q 1/68* (2006.01)
*G01N 33/53* (2006.01)
*G01N 33/00* (2006.01)
*G01N 15/06* (2006.01)
*G01N 30/96* (2006.01)

(52) U.S. Cl.
USPC .......... 435/283.1; 435/6.1; 435/7.1; 435/7.92; 435/287.2; 422/68.1; 422/69

(58) Field of Classification Search
USPC ................. 435/6.1, 7.1, 7.92, 283.1, 287.2; 422/68.1, 69, 502
See application file for complete search history.

(56) References Cited

U.S. PATENT DOCUMENTS

| | | |
|---|---|---|
| 2002/0008028 A1 | 1/2002 | Jacobson et al. |
| 2005/0069900 A1 | 3/2005 | Lentrichia |
| 2006/0177940 A1 | 8/2006 | Furst |
| 2007/0026533 A1 | 2/2007 | Sundararajan et al. |
| 2007/0042406 A1* | 2/2007 | Yantz et al. ................ 435/6 |
| 2009/0014360 A1 | 1/2009 | Toner et al. |
| 2009/0181411 A1* | 7/2009 | Battrell et al. ............. 435/7.92 |

OTHER PUBLICATIONS

Anderson, L., et al., The human plasma proteome, Mol. & Cell. Pro. 2002, 1: 845-867.
Ray, S., et al., Classification and prediction of clinical Alzheimer's diagnosis based on plasma signaling proteins, Nature Medicine 2007, 13: 1359-1362.
Kamat, A., et al., Plasma cell-free DNA in ovarian cancer, Cancer 2010, 116: 1918-1925.
Fan, R., et al., Integrated barcode chips for rapid, multiplexed analysis of proteins in microliter quantities of blood, Nature Biotechnology 2008, 26: 1373-1378.

(Continued)

*Primary Examiner* — Narayan Bhat
(74) *Attorney, Agent, or Firm* — Steinfl & Bruno LLP

(57) ABSTRACT

Provided herein is a microfluidic device and related method for controlling flow of different fluid components of a fluid. The microfluidic device comprises an input channel, focusing channel and an assaying channel. The microfluidic device is adapted to separate a fluid into at least two fluid components, and is further adapted to detect a target material comprised within one of the fluid components. The method comprises providing a channel, the channel having a dimension which is a function of a dimension of one of the fluid components and deliver the fluid through the channel at a set flow rate.

22 Claims, 17 Drawing Sheets

(56) References Cited

OTHER PUBLICATIONS

Gervais, et al., Toward one-step point-of-care immunodiagnostics using capillary-driven microfluidics and PDMS substrates, Lab on a Chip 2009, 9: 3330-3337.

Martinez, A.W., et al., Patterned Paper as a Platform for Inexpensive, Low-Volume, Portable Bioassays, Angew. Chem. Int. Ed. 2007, 46: 1318-1320.

Posthuma-Trumple, G., et al., Lateral flow (immune)assay: its strengths, weaknesses, opportunities and threats. A literature survey, Anal. Bioanal. Chem. 2009, 393: 569-582.

Qin, L., et al., Self-powered microfluidic chips for multiplexed protein assays from whole blood, Lab on a Chip 2009, 9: 2016-2020.

Shin, Y., et al., Chemistries for patterning robust DNA microbarcodes enable multiplex assays of cytoplasm proteins from single cancer cells, ChemPhysChem 2010, 11: 3063-3069.

Zheng, G., et al., Multiplexed electrical detection of cancer markers with nanowire sensor arrays, Nature Biotechnology 2005, 23: 1294-1301.

Bailey, R., et al., DNA-encoded antibody libraries: A unified platform for multiplexed cell sorting and detection of genes and proteins, JACS 2007, 129: 1959-1967.

Boozer, C., et al., DNA-directed protein immobilization for simultaneous detection of multiple analytes by surface plasmon resonance biosensor, Anal. Chem. 2006, 78: 1515-1519.

Niemayer, C., et al., Functional devices from DNA and proteins, Nanotoday 2007, 2: 42-52.

Cherukat, P., et al., The inertial lift on a rigid sphere in a linear shear flow field near a flat wall, J. Fluid Mech. 1994, 263: 1-18.

Yamada, M., et al., Pinched flow fractionation: Continuous size separation of particles utilizing a laminar flow profile in a pinched microchannel, Anal. Chem. 2004, 76: 5465-5471.

Hur, S., et al., Sheathless inertial cell ordering for extreme throughput flow cytometry, Lab on a Chip 2010, 10: 274-280.

Wang, J., et al., Vortex-assisted DNA delivery, Lab on a Chip 2010, 10: 2057-2061.

Svanes, K., et al., Variations in small blood vessel hematocrits produced in hypothermic rats by micro-occlusion, Microvas. Res. 1968, 1: 210-220.

Fung, Y., Stochastic flow in capillary blood vessels, Microvas. Res. 1973, 5: 34-48.

Yang, S., et al., A microfluidic device for continuous, real time blood plasma separation, Lab on a Chip 2006, 6: 871-880.

Nathan, C., et al., Activation of human macrophages, J. Exp. Med. 1984, 160: 600-605.

Luster, A., Chemokines—chemotactic cytokines that mediate inflammation, The New England Journal of Medicine 1998, 436-445.

Kaur, B., et al., Hypoxia and the hypoxia-inducible-factor pathway in glioma growth and angiogenesis, Neuro-Oncology 2005, 7: 134-153.

Hamirani, Y., et al., Markers of inflammation and coronary artery calcification: A systemic review, Atherosclerosis 2008, 201: 1-7.

Zimmermann, M., et al., Modeling and optimization of high-sensitivity, low-volume micorfluidic-based surface immunoassays, Biomed. Microdev. 2005, 7: 99-110.

Wang, J., et al., Detection of kinase translocation using microfluidic electroporative flow cytometry, Anal. Chem. 2008, 80: 1087-1093.

Kim, S., et al., Simple route to hydrophilic microfluidic chip fabrication using an ultraviolet (UV)-cured polymer, Adv. Func. Mat. 2007, 17: 3493-3498.

Dupont, E., et al., NOA 63 as a UV-curable material for fabrication of microfluidic channels with native hydrophilicity, Micro. Eng. 2010, 87: 1253-1255.

Di Carlo, D., et al., Continuous inertial focusing, ordering, and separation of particles in microchannels, PNAS 2007, 104: 18892-18897.

Edd, J., et al., Controlled encapsulation of single-cells into monodisperse picolitre drops, Lab on a Chip 2008, 8: 1262-1264.

Sudarsan, A., et al., Multivortex micromixing, PNAS 2006, 103: 7228-7233.

PCT International Search Report mailed Apr. 12, 2012 on for PCT Application No. PCT/US2011/052803 filed on Sep. 22, 2011 in the name of California Institute of Technology et al.

PCT Written Opinion mailed Apr. 12, 2012 on for PCT Application No. PCT/US2011/052803 filed on Sep. 22, 2011 in the name of California Institute of Technology et al.

DuPont, E., et al., NOA 63 as a UV-curable material for fabrication of microfluidic channels with native hydrophilicity, Microelec. Eng. 2010, 87: 1253-1255.

\* cited by examiner

| Name | Sequence | $T_m$ | SEQ ID NO: |
|------|----------|-------|------------|
| A | 5'- AAA AAA AAA AAA AAT CCT GGA GCT AAG TCC GTA-3' | 57.9 | 1 |
| A' | 5'NH3- AAA AAA AAA AAA ATA CGG ACT TAG CTC CAG GAT-3' | 57.2 | 2 |
| B | 5'-AAA AAA AAA AAA AGC CTC ATT GAA TCA TGC CTA-3' | 57.4 | 3 |
| B' | 5'NH3-AAA AAA AAA AAA ATA GGC ATG ATT CAA TGA GGC-3' | 55.9 | 4 |
| C | 5'- AAA AAA AAA AAA AGC ACT CGT CTA CTA TCG CTA -3' | 57.6 | 5 |
| C' | 5'NH3-AAA AAA AAA ATA GCG ATA GTA GAC GAG TGC-3' | 56.2 | 6 |
| D | 5'-AAA AAA AAA AAA AAT GGT CGA GAT GTC AGA GTA-3' | 56.5 | 7 |
| D' | 5'NH3-AAA AAA AAA ATA CTC TGA CAT CTC GAC CAT-3' | 55.7 | 8 |
| E | 5'-AAA AAA AAA AAA AAT GTG AAG TGG CAG TAT CTA-3' | 55.7 | 9 |
| E' | 5'NH3-AAA AAA AAA ATA GAT ACT GCC ACT TCA CAT-3' | 54.7 | 10 |
| F | 5'-AAA AAA AAA AAA AAT CAG GTA AGG TTC ACG GTA-3' | 56.9 | 11 |
| F' | 5'NH3-AAA AAA AAA ATA CCG TGA ACC TTA CCT GAT-3' | 56.1 | 12 |
| G | 5'-AAA AAA AAA AGA GTA GCC TTC CCG AGC ATT-3' | 59.3 | 13 |
| G' | 5'NH3-AAA AAA AAA AAA TGC TCG GGA AGG CTA CTC-3' | 58.6 | 14 |
| H | 5'-AAA AAA AAA AAT TGA CCA AAC TGC GGT GCG-3' | 59.9 | 15 |
| H' | 5'NH3-AAA AAA AAA ACG CAC CGC AGT TTG GTC AAT-3' | 60.8 | 16 |
| I | 5'-AAA AAA AAA ATG CCC TAT TGT TGC GTC GGA-3' | 60.1 | 17 |
| I' | 5'NH3-AAA AAA AAA ATC CGA CGC AAC AAT AGG GCA-3' | 60.1 | 18 |
| J | 5'-AAA AAA AAA ATC TTC TAG TTG TCG AGC AGG-3' | 56.5 | 19 |
| J' | 5'NH3-AAA AAA AAA ACC TGC TCG ACA ACT AGA AGA-3' | 57.5 | 20 |
| K | 5'-AAA AAA AAA ATA ATC TAA TTC TGG TCG CGG-3' | 55.4 | 21 |
| K' | 5'NH3-AAA AAA AAA ACC GCG ACC AGA ATT AGA TTA-3' | 56.3 | 22 |
| L | 5'-AAA AAA AAA AGT GAT TAA GTC TGC TTC GGC-3' | 57.2 | 23 |
| L' | 5'NH3-AAA AAA AAA AGC CGA AGC AGA CTT AAT CAC-3' | 57.2 | 24 |
| M | 5'-Cy3-AAA AAA AAA AGT CGA GGA TTC TGA ACC TGT-3' | 57.6 | 25 |
| M' | 5'NH3-AAA AAA AAA AAC AGG TTC AGA ATC CTC GAC-3' | 56.9 | 26 |

All sequences were purchased from Integrated DNA Technology (IDT) and purified through high performance liquid chromatography (HPLC).

FIG. 10

| DNA label | Barcode sequence | Name | Primary antibody | Detection antibody | Recombinant |
|---|---|---|---|---|---|
| A' | 1 | CRP | Mouse IgG2B Mab* (R&D***) | Mouse IgG2B Mab (R&D) | Sigma |
| B' | 2 | MMP3 | Goat IgG Pab** (R&D) | Goat IgG Pab (R&D) | R&D |
| C' | 3 | Serpin | Mouse IgG1 Mab (R&D) | Goat IgG Pab (R&D) | R&D |
| D' | 4 | G-CSF | Mouse IgG1 Mab (R&D) | Goat IgG Pab (R&D) | R&D |
| E' | 5 | MIF | Mouse IgG1 Mab (R&D) | Goat IgG Pab (R&D) | ProSpec |
| F' | 6 | EGF | Mouse IgG1 Mab (R&D) | Goat IgG Pab (R&D) | ProSpec |
| G' | 7 | CCL5 | Mouse IgG1 Mab (R&D) | Goat IgG Pab (R&D) | R&D |
| H' | 8 | VEGF | Mouse IgG2B Mab (R&D) | Goat IgG Pab (R&D) | R&D |
| I' | 9 | IL 8 | Mouse IgG1 Mab (Biolegend) | Mouse IgG1 Mab (Biolegend) | Biolegend |
| J' | 10 | IL-1β | Mouse IgG2b Mab (Biolegend) | Mouse IgG1 Mab (Biolegend) | Biolegend |
| K' | 11 | IP10 | Mouse IgG1 Mab (R&D) | Goat IgG Pab (R&D) | R&D |
| L' | 12 | Control | Mouse IgG1 Isotype control (R&D) | N.A. | |

\* Mab: monoclonal antibody
\*\* Pab: polyclonal antibody
\*\*\* R&D: R&D Systems

FIG. 11

SEQUENCE LISTING

```
<160> NUMBER OF SEQ ID NOS: 26

<210> SEQ ID NO 1
<211> LENGTH: 33
<212> TYPE: DNA
<213> ORGANISM: Artificial sequence
<220> FEATURE:
<223> OTHER INFORMATION: Synthetic polynucleotide

<400> SEQUENCE: 1
aaaaaaaaaa aaaatcctgg agctaagtcc gta                                  33

<210> SEQ ID NO 2
<211> LENGTH: 30
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
```

```
<222> LOCATION: (1)..(1)
<223> OTHER INFORMATION: n is adenine (A) linked to group -NH3

<400> SEQUENCE: 2
naaaaaaaaa tacggactta gctccaggat                                    30

<210> SEQ ID NO 3
<211> LENGTH: 33
<212> TYPE: DNA
<213> ORGANISM: Artificial sequence
<220> FEATURE:
<223> OTHER INFORMATION: Synthetic polynucleotide

<400> SEQUENCE: 3
aaaaaaaaaa aaagcctcat tgaatcatgc cta                                33

<210> SEQ ID NO 4
<211> LENGTH: 30
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: n is adenine (A) linked to group -NH3

<400> SEQUENCE: 4
naaaaaaaaa taggcatgat tcaatgaggc                                    30

<210> SEQ ID NO 5
<211> LENGTH: 33
<212> TYPE: DNA
<213> ORGANISM: Artificial sequence
<220> FEATURE:
<223> OTHER INFORMATION: Synthetic polynucleotide

<400> SEQUENCE: 5
aaaaaaaaaa aaagcactcg tctactatcg cta                                33

<210> SEQ ID NO 6
<211> LENGTH: 30
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: n is adenine (A) linked to group -NH3

<400> SEQUENCE: 6
naaaaaaaaa tagcgatagt agacgagtgc                                    30

<210> SEQ ID NO 7
<211> LENGTH: 33
<212> TYPE: DNA
<213> ORGANISM: Artificial sequence
<220> FEATURE:
<223> OTHER INFORMATION: Synthetic polynucleotide

<400> SEQUENCE: 7
aaaaaaaaaa aaaatggtcg agatgtcaga gta                                33

<210> SEQ ID NO 8
<211> LENGTH: 30
<212> TYPE: DNA
<213> ORGANISM: Artificial sequence
```

```
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: n is adenine (A) linked to group -NH3

<400> SEQUENCE: 8
naaaaaaaaa tactctgaca tctcgaccat                                        30

<210> SEQ ID NO 9
<211> LENGTH: 33
<212> TYPE: DNA
<213> ORGANISM: Artificial sequence
<220> FEATURE:
<223> OTHER INFORMATION: Synthetic polynucleotide

<400> SEQUENCE: 9
aaaaaaaaaa aaaatgtgaa gtggcagtat cta                                    33

<210> SEQ ID NO 10
<211> LENGTH: 30
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: n is adenine (A) linked to group -NH3

<400> SEQUENCE: 10
naaaaaaaaa tagatactgc cacttcacat                                        30

<210> SEQ ID NO 11
<211> LENGTH: 33
<212> TYPE: DNA
<213> ORGANISM: Artificial sequence
<220> FEATURE:
<223> OTHER INFORMATION: Synthetic polynucleotide

<400> SEQUENCE: 11
aaaaaaaaaa aaaatcaggt aaggttcacg gta                                    33

<210> SEQ ID NO 12
<211> LENGTH: 30
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: n is adenine (A) linked to group -NH3

<400> SEQUENCE: 12
naaaaaaaaa taccgtgaac cttacctgat                                        30

<210> SEQ ID NO 13
<211> LENGTH: 30
<212> TYPE: DNA
<213> ORGANISM: Artificial sequence
<220> FEATURE:
<223> OTHER INFORMATION: Synthetic polynucleotide

<400> SEQUENCE: 13
aaaaaaaaaa gagtagcctt cccgagcatt                                        30
```

```
<210> SEQ ID NO 14
<211> LENGTH: 30
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: n is adenine (A) linked to group -NH3

<400> SEQUENCE: 14
naaaaaaaaa aatgctcggg aaggctactc                                    30

<210> SEQ ID NO 15
<211> LENGTH: 30
<212> TYPE: DNA
<213> ORGANISM: Artificial sequence
<220> FEATURE:
<223> OTHER INFORMATION: Synthetic polynucleotide

<400> SEQUENCE: 15
aaaaaaaaaa attgaccaaa ctgcggtgcg                                    30

<210> SEQ ID NO 16
<211> LENGTH: 30
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: n is adenine (A) linked to group -NH3

<400> SEQUENCE: 16
naaaaaaaaa cgcaccgcag tttggtcaat                                    30

<210> SEQ ID NO 17
<211> LENGTH: 30
<212> TYPE: DNA
<213> ORGANISM: Artificial sequence
<220> FEATURE:
<223> OTHER INFORMATION: Synthetic polynucleotide

<400> SEQUENCE: 17
aaaaaaaaaa tgccctattg ttgcgtcgga                                    30

<210> SEQ ID NO 18
<211> LENGTH: 30
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: n is adenine (A) linked to group -NH3

<400> SEQUENCE: 18
naaaaaaaaa tccgacgcaa caatagggca                                    30

<210> SEQ ID NO 19
<211> LENGTH: 30
<212> TYPE: DNA
<213> ORGANISM: Artificial sequence
<220> FEATURE:
<223> OTHER INFORMATION: Synthetic polynucleotide

<400> SEQUENCE: 19
```
aaaaaaaaaa tcttctagtt gtcgagcagg         30

<210> SEQ ID NO 20
<211> LENGTH: 30
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: n is adenine (A) linked to group -NH3

<400> SEQUENCE: 20
naaaaaaaaa cctgctcgac aactagaaga         30

<210> SEQ ID NO 21
<211> LENGTH: 30
<212> TYPE: DNA
<213> ORGANISM: Artificial sequence
<220> FEATURE:
<223> OTHER INFORMATION: Synthetic polynucleotide

<400> SEQUENCE: 21
aaaaaaaaaa taatctaatt ctggtcgcgg         30

<210> SEQ ID NO 22
<211> LENGTH: 30
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: n is adenine (A) linked to group -NH3

<400> SEQUENCE: 22
naaaaaaaaa ccgcgaccag aattagatta         30

<210> SEQ ID NO 23
<211> LENGTH: 30
<212> TYPE: DNA
<213> ORGANISM: Artificial sequence
<220> FEATURE:
<223> OTHER INFORMATION: Synthetic polynucleotide

<400> SEQUENCE: 23
aaaaaaaaaa gtgattaagt ctgcttcggc         30

<210> SEQ ID NO 24
<211> LENGTH: 30
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: n is adenine (A) linked to group -NH3

<400> SEQUENCE: 24
naaaaaaaaa gccgaagcag acttaatcac         30

<210> SEQ ID NO 25
<211> LENGTH: 30
<212> TYPE: DNA
<213> ORGANISM: Artificial sequence

```
-continued

<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: n is adenine (A) linked to fluorophore Cy3

<400> SEQUENCE: 25
naaaaaaaaa gtcgaggatt ctgaacctgt                                        30

<210> SEQ ID NO 26
<211> LENGTH: 30
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: n is adenine (A) linked to group -NH3

<400> SEQUENCE: 26
naaaaaaaaa acaggttcag aatcctcgac                                        30
```

LATERAL FLOW MICROFLUIDIC ASSAYING DEVICE AND RELATED METHOD

CROSS REFERENCE TO RELATED APPLICATIONS

This application claims priority to U.S. Provisional Application entitled "A Self-Powered, One-Step Chip for Rapid Quantitative and Multiplexed Detection of Proteins form Pin-Pricks of Whole Blood", Ser. No. "61/385,432", filed on Sep. 22, 2010, the disclosure of which is incorporated herein by reference in its entirety.

STATEMENT OF GOVERNMENT GRANT

This invention was made with government support under CA119347 awarded by the National Institute of Health. The government has certain rights in the invention.

FIELD

The present disclosure relates to microfluidic device and related methods for controlling flow of fluid components of a fluid sample.

SUMMARY

Provided herein are microfluidic device and related method for controlling flow of fluid components of a fluid sample. In some embodiments herein described, the controlling of flow results in separation of the fluid components of the sample and allows detection of one or more target materials comprised in at least one of the fluid components of the sample.

According to a first aspect of the disclosure, a microfluidic device for controlling flow of a first fluid component and a second fluid component in a fluid sample is described. The first fluid component comprises at least one target. The microfluidic device comprises an inlet channel for introducing the fluid sample into the microfluidic device, a focusing channel in fluidic communication with the inlet channel and an assaying channel in fluidic communication with the focusing channel. The assaying channel carries at least one capture agent or component thereof, the at least one capture agent or component thereof attached to the assaying channel, the at least one capture agent or component thereof having a binding affinity for the target. The focusing channel is adapted to move a second fluidic component of the fluid sample in a distance away from surfaces of the assaying channel and keep the first component in contact with the at least one capture agent or component thereof.

According to a second aspect of the disclosure, a method for separating a fluid into a first component and a second component is described. The first component of the fluid comprises particles within a certain size range. The method comprises providing a channel, the channel having a dimension which is a function of the size range of the particles; and delivering the fluid through the channel at a set flow rate.

The microfluidic device and method herein described allow in several embodiments separation, isolation and/or purification of fluid components of a fluid sample, such as separation of blood plasma from blood cells in a whole blood sample.

The microfluidic device and method herein described also allow in several embodiments rapid, quantitative and multiplex capturing and detection of targets from a separated fluid component, such as detection of one or more proteins of interest comprised in a blood plasma.

The microfluidic device and method can be used in application where rapid detection of a target, such as a pathogenic macromolecule, from a biological sample is desired, including but not limited to, medical application, such as point-of-care diagnosis, biological analysis, diagnostics including but not limited to clinical applications.

The details of one or more embodiments of the disclosure are set forth in the accompanying drawings and the description below. Other features, objects, and advantages will be apparent from the description and drawings, and from the claims.

BRIEF DESCRIPTION OF DRAWINGS

The accompanying drawings, which are incorporated into and constitute a part of this specification, illustrate one or more embodiments of the present disclosure and, together with the description of example embodiments, serve to explain the principles and implementations of the disclosure.

FIG. 10 shows a table of the ssDNA oligomers having SEQ ID NO: 1 to SEQ ID NO: 26 which are used for assembling the barcode for an ELISA assay, according to one embodiment of the present disclosure.

FIG. 11 shows a table of the antibody pairs used in the ELISA barcode assay, according to one embodiment of the present disclosure.

DETAILED DESCRIPTION

Figure 1:
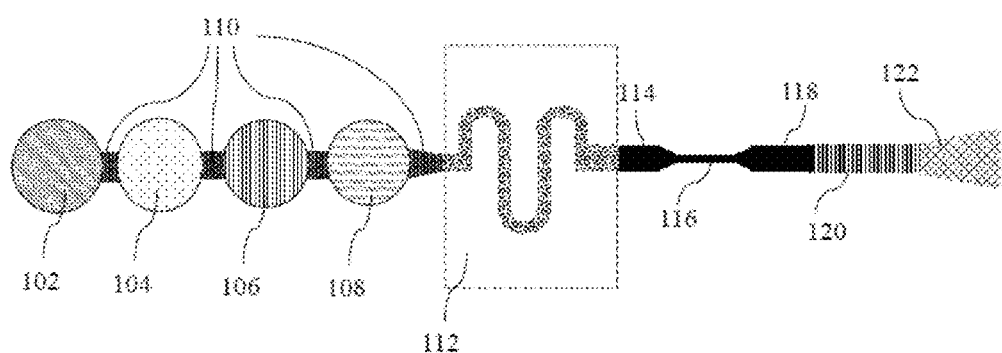
FIG. 1 depicts the top view of the microfluidic chip, according to one embodiment of the present disclosure.

Described herein are a microfluidic device and related method for controlling flow of different fluid components of a fluid sample.

The term "fluid", "fluidics" or "fluid component" as used herein indicates a substance that continually flows under an applied shear stress. In the sense of the present disclosure, fluid can be liquids, gases, or solids, such as plasma, colloids, suspension or slurry of micro-particles, such as cells etc. Exemplary types of fluid according to the present disclosure include but are not limited to air, reagent solutions, and a blood sample, including blood cells, serum and plasma.

The term "sample" as used herein indicates a limited quantity of something that is indicative of a larger quantity of that something, including but not limited to fluids from a biological environment, specimen, cultures, tissues, commercial recombinant proteins, synthetic compounds or portions thereof.

In some embodiments herein described, the fluid sample comprises multiple fluid components. At least one of the components comprises a fluidic suspension of particles. By way of example, a blood sample is described in connection with the present microfluidic device in details below, although the present microfluidic device and method can also be employed to handle, process, and/or analyze many other types of fluid samples, as would recognized by one skilled in the art upon reading the present disclosure.

Blood contains the most complete version of the human proteome, and so provides a rich and convenient source of information for disease diagnostics. Conventional clinical blood protein diagnostic measurements are quantitative, but also time-consuming. They require multiple steps, a significant amount of blood sample, and can be awkward to multiplex when assaying large panels of protein biomarkers, although there is recent progress in this area. By contrast, lateral flow point-of-care (LF-POC) devices, which are widely used for rapid detection of blood biomarkers from patients in developing world settings, are inexpensive, self-contained, and simple to operate, and usually require only small amount of blood samples. However, they are neither quantitative nor multi-parametric. In several embodiments, devices and methods herein described encompass many of the advantages of both standard and POC protein diagnostics, and/or provide multiplexed measurements.

In some embodiments, a microfluidic chip is described. In particular, in some embodiments, the microfluidic chip controls flow of different fluid components of a fluid sample to separate the controlled components into different flowing streams. In some of those embodiments, the control of fluid components is performed to allow detection of one or more targets comprised in one of the fluid components.

In several embodiments, the microfluidic chip comprises an inlet channel for introducing the fluid sample into the chip, a focusing channel in fluidic communication with the inlet channel and an assaying channel in fluidic communication with the focusing channel. The configuration of the focusing channel, inlet channel and assaying channel is such that flow of different fluid components is controlled to separate the fluid components one from the other.

In particular, in some embodiments, the configuration of the focusing channel inlet channel and assaying channel can be adapted to move a fluidic component of the fluid sample in a distance away from surfaces of the assaying channel and keep a different fluidic component of the fluid sample proximate to the surfaces of the assaying channel.

In some embodiments, the inlet channel can comprise inlet ports or chambers for receiving or loading one or more fluid input into the microfluidic chip. The inlet channel can further comprise mechanisms for processing the fluid input, such as filtering and/or mixing a fluid sample and/or reagent. In some embodiments, the inlet channel can further comprise mechanisms adapted to load more than one fluid in a pre-determined sequential order.

In some embodiments, the focusing channel is adapted to receive the fluid input from the inlet channel and separate the fluid into at least two fluid components before the fluid reaches the assaying channel. In some of those embodiments, the assaying channel carries at least one capture agent on its surfaces, which has a binding affinity for a target material comprised in one of the fluid components.

The term "capture agent" as used herein indicates a compound that can specifically bind to a target. For example, disclosed capture agents can be configured to specifically bind to a target. Exemplary capture agents comprise organic molecules, such as polypeptides, polynucleotides and other non-polymeric molecules that are identifiable to a skilled person.

In some embodiments, the focusing channel is adapted to move at least one fluidic component of the fluid input in a distance away from surfaces of the assaying channel and keep at least one other component in contact with the capture agents located on the surface of the assaying channel. In particular, in some embodiments, the dimension of the focusing channel is proportional to a dimension of one of the fluid components.

In some embodiments, flow of the fluid through the microfluidic chip is driven by an absorbing material in contact with the fluid at the end of the assaying channel, which is adapted to draw the fluid from the inlet towards the assaying channel.

Exemplary embodiments of the microfluidic chip and of related methods and systems herein described are illustrate in FIGS. 1 to 17 and described in detail below. However, it is to be understood that the specific embodiments as described in the figures are intended to provide examples of possible embodiments of the disclosure and it will be apparent to one skilled in the art that the microfluidic chip or device as herein described can be carried out using a large number of variations of the devices, device components, methods steps set forth in the present description.

In particular, FIG. 1 shows the top view of the microfluidic chip, according to one embodiment of the present disclosure. The microfluidic chip comprises four loading chambers (102, 104, 106, 108). Filter channels (110) connect chambers (102, 104, 106, 108). In a further embodiment, the filter channels (110) can be configured as channels with arrays of posts. In some, embodiments, the filter channel between the chamber (108) and the mixing channel (112) has more compact posts than the other three filter channels which is typically associated with an increased filtering with respect to other configuration. In general, more compact posts can be used to minimize clogging of the narrow focusing channel (116) due impurities originating in chambers (102, 104, 106, 108). In the illustration of FIG. 1, the microfluidic chip also comprises a mixing channel (112).

In a further embodiment, mixing channel (112) is a serpentine. In particular, in some of those embodiments, mixing channel (112) incorporates Dean vortices at one or more turns of the serpentine for mixing the fluid flowing through the mixing channel (112). In some embodiments, Dean vortices can be included at each turn of mixing channel (112) in serpentine configuration. In the illustration of FIG. 1, mixing channel (112) is connected to the focusing channel (116), which comprises a channel that is narrower that the channels immediately preceding (114) and immediately following (118) channel (116).

In the illustration of FIG. 1, focusing channel (116) confines particles in the fluid (such as blood cells in a blood sample) to flow through a central stream of focusing channel (116). Thus, when the fluid reaches the following wide channel (118), the particles in the fluid are kept in a distance away from surfaces of the wide channel (118) and surfaces of the following assaying channel (120).

In some embodiments, the assaying channel (120) is adapted for binding of certain target materials in the fluid. In particular, in some of those embodiments, the assaying channel (120) is adapted to bind the target material through agents suitable to be used in an affinity binding assay.

In the illustration of FIG. 1, the microfluidic chip also comprises an outlet (122) that is connected to the assaying channel (120). The outlet (122) allows for easy insertion of an absorbent material (e.g. a filter paper) to the channels.

The term "target", "target material" or "target analyte" as used herein refers to a molecule or compound of interest that is to be analyzed, e.g., a nucleotide, an oligonucleotide, or a protein. The target or target material could be a small molecule, biomolecule, or nanomaterial such as but not necessarily limited to a small molecule that is biologically active, nucleic acids and their sequences, peptides and polypeptides, as well as nanostructure materials chemically modified with biomolecules or small molecules capable of binding to molecular probes such as chemically modified carbon nanotubes, carbon nanotube bundles, nanowires, nanoclusters or nanoparticles. The target material can comprise or be conjugated with a detectable label, such as a fluorescent label.

The term "binding" as used herein indicates an attractive interaction between two entities which results in a stable association of the entities in which the entities are in close proximity to each other. If each entity is comprised in a molecule the result of binding is typically formation of a molecular complex. Attractive interactions in the sense of the present disclosure includes both non-covalent binding and, covalent binding. Non-covalent binding as used herein indicates a type of chemical bond, such as protein-protein interaction, that does not involve the sharing of pairs of electrons, but rather involves more dispersed variations of electromagnetic interactions. Non-covalent bonding includes ionic bonds, hydrophobic interactions, electrostatic interactions, hydrogen bonds, and dipole-dipole bonds. Electrostatic interactions include association between two oppositely charged entities.

In some embodiments, the channel structures of the microfluidic chip are formed by bonding a polydimethylsiloxane (PDMS) replica on a glass slide that has a pre-formed detection assay. The fabrication process starts with photolithography. A high-resolution chrome mask is used for photolithography; its features are replicated on a 4-inch silicon wafer with negative photoresist (SU-8 2025, Microchem), yielding a master for molding PDMS (ESI Methods). The pre-cure PDMS mixture of part A and part B (10:1; RTV 615, General Electric) is poured to the master and incubated at 80° C. for 40 min. The cured PDMS is cut off from the master and punched for access holes. Afterwards, the PDMS replica is cleaned by rinsing with isopropyl and deionized (DI) water followed with blow dry. After subsequent treatment with oxygen plasma at 25 W for 100 s to render the surface hydrophilic, the PDMS replica is bonded to a glass slide that has a pre-formed detection assay.

Figure 17:
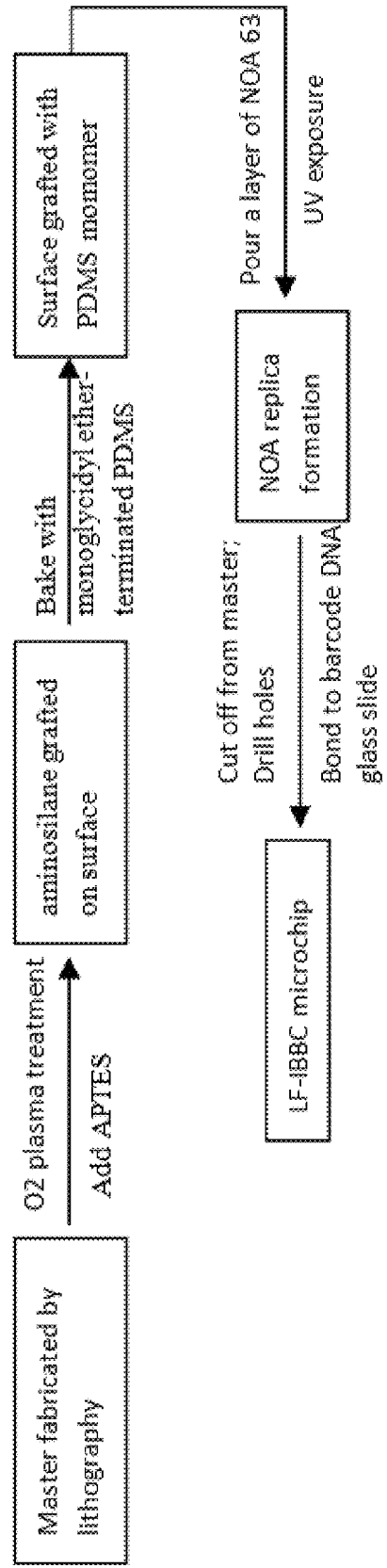
FIG. 17 depicts exemplary flow chart for the fabrication process of the channel structures of the microfluidic chip.

In some embodiments, the channel structures of the microfluidic chip are formed by bonding a Norland Optical Adhesive 63® (NOA 63) replica on a glass slide that has a pre-formed detection assay. As shown in FIG. 17, a high-resolution chrome mask is used for photolithography; its features are replicated on a 4-inch silicon wafer with negative photoresist (SU-8 2025, Microchem), yielding a master for molding NOA 63 (Norland). Then, a layer of aminosilane is grafted on the surface of the master mold by $O_2$ plasma activation at 25 W for 30 s, followed by immersion in 2% 3-(aminopropyl triethoxysilane) (APTES, Sigma-Aldrich) in acetone for 10 min. The master is washed sequentially with isopropanol and DI water before an N2 blow dry. A thin layer of monoglycidyl ether-terminated PDMS (Sigma-Aldrich) is spun with a speed of 1000 rpm for 30 s on the modified master, and subsequently incubated at 80° C. for 4 hours.

The master is then cleaned with isopropanol and dried under streaming N2. The resulting PDMS monolayer on the master prevents NOA 63 from sticking to the surface. Next, an aluminum plate with cutouts is fitted over the silicon master such that the SU-8 features are exposed through the cutouts. NOA 63 is poured into the cutouts, and the assembly is treated for 5 minutes with UV exposure before the NOA replica is peeled off. The replica is further processed by drilling chamber holes with a standard drill press and trimmed to appropriate dimensions. UV treatment is performed again to render the surface permanently hydrophilic. Finally, the NOA replica is bonded to a glass slide that has a pre-formed detection assay.

In some embodiments, the assaying channel (120) of FIG. 1 provides capture agents suitable for binding one or more target materials of the fluid sample. Subsequently, additional reagents flow through the assaying channel (120) to detect the bound material through an affinity binding assay. Almost all modes of affinity binding assays can be employed to the present invention for detecting presence and/or abundance of a target in a sample, which include both soluble and solid phase formats. A specific example of a soluble phase affinity binding assay is immunoprecipitation using a target selective antibody or other capture agent. Specific examples of solid phase affinity binding assay include immunohistochemical binding assays, immunoaffinity binding assays such as an Enzyme-linked immunosorbent assay (ELISA) and radioimmune assay (RIA). Other solid phase affinity binding assays are known to those skilled in the art and are applicable to the methods of the present invention. In several of those binding assays, the capture agents used are antibodies.

The term "antibody" as used herein refers to a protein of the kind that is produced by activated B cells after stimulation by an antigen and can bind specifically to the antigen promoting an immune response in biological systems. Full antibodies typically consist of four subunits including two heavy chains and two light chains. The term antibody includes natural and synthetic antibodies, including but not limited to monoclonal antibodies, polyclonal antibodies or fragments thereof. Exemplary antibodies include IgA, IgD, IgG1, IgG2, IgG3, IgM and the like. Exemplary fragments include Fab Fv, Fab' F(ab')2 and the like. A monoclonal antibody is an antibody that specifically binds to and is thereby defined as complementary to a single particular spatial and polar organization of another biomolecule which is termed an "epitope". In some forms, monoclonal antibodies can also have the same structure. A polyclonal antibody refers to a mixture of different monoclonal antibodies. In some forms, polyclonal antibodies can be a mixture of monoclonal antibodies where at least two of the monoclonal antibodies binding to a different antigenic epitope. The different antigenic epitopes can be on the same target, different targets, or a combination. Antibodies can be prepared by techniques that are well known in the art, such as immunization of a host and collection of sera (polyclonal) or by preparing continuous hybridoma cell lines and collecting the secreted protein (monoclonal).

Although many affinity binding assays are formatted for use with an antibody binding molecule that is specific for the target analyte of interest, other capture agents can be additionally or alternatively used in binding assays that can be performed in connection with devices and methods herein described. Exemplary capture agents include but are not restricted to macromolecules such as aptamers, polypeptides, peptides, polynucleotides, lipids and sugars as well as small molecule compounds. Methods are known in the art for identifying such molecules which bind specifically to a particular analyte or ligand and include, for example, surface display libraries and combinatorial libraries. Thus, for a molecule other than an antibody to be used in an affinity binding assay, all that is necessary is for the binding entity or agent to exhibit specific binding activity for the target analyte.

The term "aptamers" as used here indicates oligonucleic acid or peptide molecules that bind a specific target. In particular, nucleic acid aptamers can comprise, for example, nucleic acid species that have been engineered through repeated rounds of in vitro selection or equivalently, SELEX (systematic evolution of ligands by exponential enrichment) to bind to various molecular targets such as small molecules, proteins, nucleic acids, and even cells, tissues and organisms. Aptamers are useful in biotechnological and therapeutic applications as they offer molecular recognition properties that rival that of the antibodies. Peptide aptamers are peptides that are designed to specifically bind to and interfere with protein-protein interactions inside cells. In particular, peptide aptamers can be derived, for example, according to a selection strategy that is derived from the yeast two-hybrid (Y2H) system. In particular, according to this strategy, a variable peptide aptamer loop attached to a transcription factor binding domain is screened against the target protein attached to a transcription factor activating domain. In vivo binding of the peptide aptamer to its target via this selection strategy is detected as expression of a downstream yeast marker gene.

The term "polypeptide" as used herein indicates an organic linear, circular, or branched polymer composed of two or more amino acid monomers and/or analogs thereof. The term "polypeptide" includes amino acid polymers of any length including full length proteins and peptides, as well as analogs and fragments thereof. A polypeptide of three or more amino acids is also called a protein oligomer, peptide or oligopeptide. In particular, the terms "peptide" and "oligopeptide" usually indicate a polypeptide with less than 50 amino acid monomers. As used herein the term "amino acid", "amino acidic monomer", or "amino acid residue" refers to any of the twenty naturally occurring amino acids, non-natural amino acids, and artificial amino acids and includes both D an L optical isomers. In particular, non-natural amino acids include D-stereoisomers of naturally occurring amino acids (these including useful ligand building blocks because they are not susceptible to enzymatic degradation). The term "artificial amino acids" indicate molecules that can be readily coupled together using standard amino acid coupling chemistry, but with molecular structures that do not resemble the naturally occurring amino acids. The term "amino acid analog" refers to an amino acid in which one or more individual atoms have been replaced, either with a different atom, isotope, or with a different functional group but is otherwise identical to original amino acid from which the analog is derived. All of these amino acids can be synthetically incorporated into a peptide or polypeptide using standard amino acid coupling chemistries (Lam, K. S. et al., 1997). The term "polypeptide" as used herein includes polymers comprising one or more monomer, or building blocks other than an amino acid monomer. The terms monomer, subunit, or building blocks indicate chemical compounds that under appropriate conditions can become chemically bonded to another monomer of the same or different chemical nature to form a polymer. The term "polypeptide" is further intended to comprise a polymer wherein one or more of the building blocks is covalently bound to another by a chemical bond other than amide or peptide bond. In several embodiments, at least one ligand of the two or more ligands comprises one or more amino acid residues and can in particular be formed by a polypeptide. In particular, in several embodiments, at least one of the at least two ligands is a peptide comprising between three and hundred monomers, and in particular, between five and eighty monomers. In some embodiments, the peptide can comprise three to ten monomers, and in particular five to seven monomers. In some embodiments, the multi-ligand capture agent can be comprised of a protein.

The term "protein" as used herein indicates a polypeptide with a particular secondary and tertiary structure that can interact with another analyte and in particular, with other biomolecules including other proteins, DNA, RNA, lipids, metabolites, hormones, chemokines, and small molecules.

The term "polynucleotide" as used herein indicates an organic polymer composed of two or more monomers including nucleotides, nucleosides or analogs thereof. The term "nucleotide" refers to any of several compounds that consist of a ribose or deoxyribose sugar joined to a purine or pyrimidine base and to a phosphate group and that is the basic structural unit of nucleic acids. The term "nucleoside" refers to a compound (such as guanosine or adenosine) that consists of a purine or pyrimidine base combined with deoxyribose or ribose and is found especially in nucleic acids. The term "nucleotide analog" or "nucleoside analog" refers respectively to a nucleotide or nucleoside in which one or more individual atoms have been replaced with a different atom or a with a different functional group. Accordingly, the term "polynucleotide" includes nucleic acids of any length, and in particular DNA, RNA, analogs and fragments thereof. A polynucleotide of three or more nucleotides is also called "nucleotidic oligomer" or "oligonucleotide."

The wording "specific" "specifically" or "specificity" as used herein with reference to the binding of a first molecule to second molecule refers to the recognition, contact and formation of a stable complex between the first molecule and the second molecule, together with substantially less to no recognition, contact and formation of a stable complex between each of the first molecule and the second molecule with other molecules that may be present. Exemplary specific bindings are antibody-antigen interaction, cellular receptor-ligand interactions, polynucleotide hybridization, enzyme substrate interactions etc. The term "specific" as used herein with reference to a molecular component of a complex, refers to the unique association of that component to the specific complex which the component is part of. The term "specific" as used herein with reference to a sequence of a polynucleotide refers to the unique association of the sequence with a single polynucleotide which is the complementary sequence. By "stable complex" is meant a complex that is detectable and does not require any arbitrary level of stability, although greater stability is generally preferred.

The term "specific binding" or "specific interaction" is the specific recognition of one of two different binding entities for the other compared to substantially less recognition of other molecules. Generally, the molecules have areas on their surfaces or in cavities giving rise to specific recognition between the two molecules. Exemplary of specific binding are antibody-antigen interactions, enzyme-substrate interactions, polynucleotide hybridization interactions, and so forth.

The various modes of affinity binding assays, such as immunoaffinity binding assays, include, for example, immunohistochemistry methods, solid phase ELISA and RIA as well as modifications thereof. Such modifications thereof include, for example, capture assays and sandwich assays as well as the use of either mode in combination with a competition assay format. The choice of which mode or format of immunoaffinity binding assay to use will depend on the intent of the user. Such methods can be found described in common laboratory manuals such as Harlow and Lane, Using Antibodies: A Laboratory Manual, Cold Spring Harbor Laboratory Press, New York (1999).

In some embodiments, capture agents suitable for use in an affinity binding assay of the assaying channel (120) can be arranged in various patterns according to a desired experimental design and corresponding reading. In particular, in an embodiment, capture agents can be configured in a barcode pattern. In particular, the barcode pattern can comprise multiple stripes immobilized on a surface of the assaying channel (120), each stripe comprising one or more capture agents able to specifically recognize and bind to one or more particular targets in the fluid sample, and is thus suitable for detecting the one or more targets in the sample. Procedures for fabricating a surface including capture agents in an exemplary barcode pattern are exemplified below.

Figure 7:
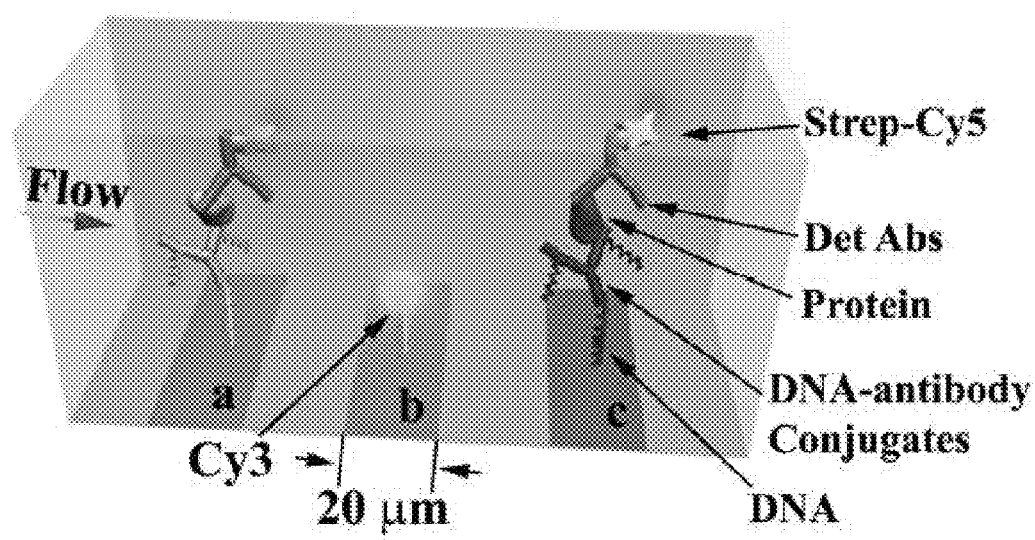
FIG. 7 illustrates affinity binding of various molecules during an assay which is arranged in a barcode pattern, according to one embodiment of the present disclosure.
Figure 8:
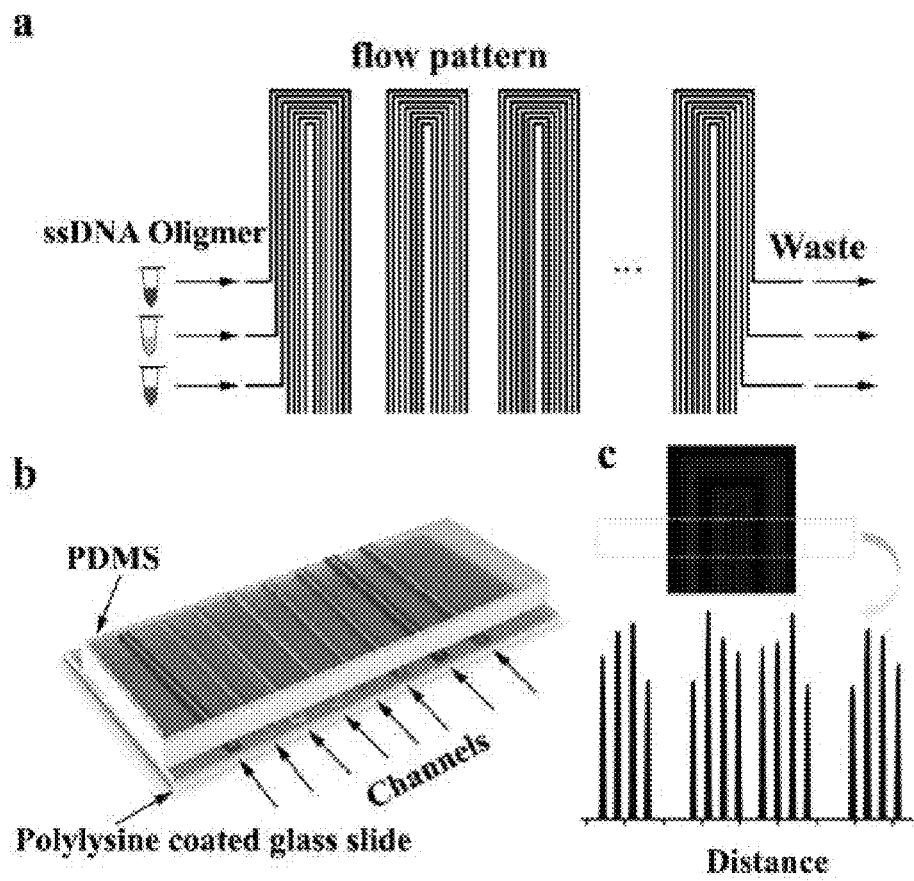
FIG. 8 depicts a flow pattern for a single-stranded DNA (ssDNA) oligomer barcode, a microfluidic structure for fabricating the barcode and results of testing the barcode with an affinity binding assay, according to one embodiment of the present disclosure.

The barcode, as illustrated in FIG. 7, comprises 20-μm wide stripes at a 50-μm pitch. The barcode has ten times higher density than standard, spotted microarrays.

According to one embodiment of the present disclosure, the fabrication of the barcode starts with creating a PDMS replica that has flow patterns (FIG. 8a) for the barcode strips. The fabrication of the PDMS replica is similar to the process described above for fabricating the PDMS replica for the channel structures. Next, the PDMS replica is bonded to PDMS to a polylysine glass slide with thermal treatment at 80° C. for 1 hour. FIG. 8b shows the glass slide with the PDMS replica. Each of the channels formed by the PDMS replica and the polylysine glass slide is filled with a unique single-stranded DNA (ssDNA) sequence. Then, the slide is placed in a desiccator to allow solvents (such as water and/or DMSO) to evaporate from the channel. Next, the slide is incubated at 80° C. for 4 hours. This thermal process cross-links the ssDNA to the surface of the polylysine glass slide. Then, the PDMS replica is peeled off the glass slide. Subsequently, the glass slide is cleaned with DI water to remove un-bonded ssDNA and other solids. Finally the glass slide (containing ssDNA barcode stripes) is dried by $N_2$ blowing and preserved in a desiccator.

FIG. 8c shows a diagram of a fabricated DNA barcode (top) and testing of such barcode through an affinity binding assay using Cy3-labeled complementary ssDNA (bottom). The testing result (bottom) shows fluorescence emission of the Cy3 label from the flow pattern of the strips, indicating binding of the complementary ssDNA to the ssDNA that is immobilized in the stripes. Accordingly, the Cy3-labeled complementary DNA can be used in some embodiments to confirm the presence and quality of the DNA component of the barcode, prior to real assay tests.

After the barcode is created on the polylysine glass slide, a PDMS replica having channel structures is bonded to the polylysine glass slide through a similar procedure described above.

According to other embodiments of the present disclosure, additional capture agents can be further assembled onto the DNA barcode to covert the barcode into a format that is suitable for detecting various biological entities, such as biochemical molecules and/or compounds. Such assembly can be achieve through the use of the DNA-encoded chemical libraries (DEL) technology, which involves the conjugation of a suitable capture agent with a single-stranded polynucleotide that is capable of hybridizing to the ssDNA component of the DNA barcode already fabricated on the surface of the assaying channel (120).

Figure 9:
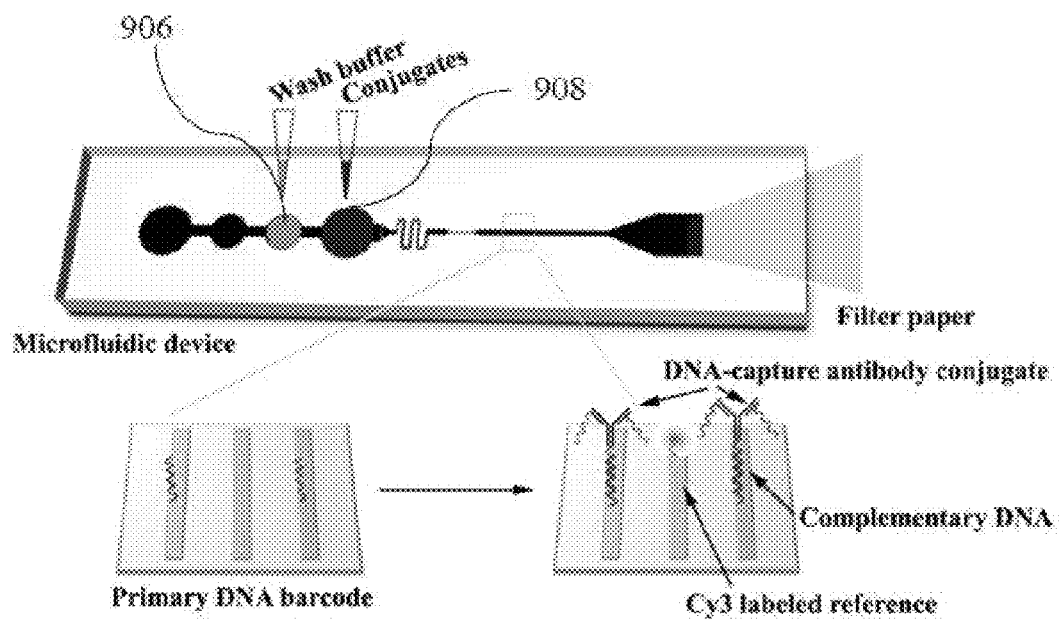
FIG. 9 illustrates the process for converting a DNA barcode to an antibody barcode suitable for an ELISA assay using the DEL technique, according to one embodiment of present disclosure.

FIG. 9 shows an exemplary procedure of fabricating a barcode suitable for an ELISA assay according to an embodiment herein described. As shown in FIG. 9, 10 μL DNA-antibody conjugates and 10 μL wash buffer (3% BSA in PBS) are added to chambers 908 and 906, respectively. Subsequently, the conjugates flow through the assaying channel and are assembled onto the primary DNA barcodes via DNA hybridization. Wash buffer then flows through the assaying channel and rinse away any un-bound DNA-antibody conjugates.

The performance of the affinity binding assay can be affected by various factors. Study shows that the assay sensitivity measured as the number of analyte molecules captured during the assay can depend on the affinity and/or specificity between a target analyte and a capture agent provided in the assaying channel (measured as the binding constant/coefficient), presence of other components of sample matrices that can block or compete for the binding to the capture agent, possible target analyte concentrations in the sample, and assaying time that allows for recognition and association of the target analyte to the capture agent.

Accordingly, the choice of a suitable assaying time that allows for sufficient amount of binding between the target analyte and capture agent to achieve satisfying assay sensitivity will depend on the intent of the user, which includes but is not limited to, the type of sample to be analyzed, requirement for assay speed, and requirement for assay sensitivity etc.

Relationship and relative dependency among these factors are reported in Zimmermann, M. et al. "Modeling and Optimization of High Sensitivity, Low Volume Microfluidic-Based Surface Immunoassays." Biomedical Microdevices 7:2, 99-110, 2005, pp. 100-101, of which the disclosure in incorporated by reference in its entirety. Reference is made, in particular, to a passage of Zimmermann, reported in the following paragraphs.

"The flow of a liquid in a region over time t is characterized by a velocity vector field $\bar{u}$ a pressure p and a density ρ. For laminar, incompressible and viscous fluids the density is constant. The flow is described by the Navier-Stokes partial differential equation system $$\frac{\partial}{\partial t}\bar{u} + (\bar{u} \cdot grad)\bar{u} + grad\, p = \frac{1}{Re}\Delta\bar{u} + \bar{g} \quad (1)$$

$$div\,\bar{u} = 0 \quad (2)$$

in dimensionless form with the Reynolds number Re and external forces $\vec{g}$. External forces such as gravity can be neglected in such miniaturized systems. For Re<<2100, flow is considered to be laminar and has a characteristic parabolic flow profile with zero flow velocity at the channel walls and peak flow velocity in the channel center. Here, Re is ~0.07 for the maximum flow rates considered.

The bulk concentration C of a solute in a given solution is described by the Convection-Diffusion equation of the form $$\frac{\partial C}{\partial t} + \vec{u} \cdot gradC = D\Delta C + \Theta(t, x, y, C)$$

with a diffusion coefficient D, a source term $\Theta$ and the identical velocity vector field $\vec{\mu}$ given in equation (1). We have applied the Stokes-Einstein-relation $$D = \frac{kT}{6\pi\eta R_h},$$

with the hydrodynamic radius $R_h$, the analyte viscosity $\eta$ and the Boltzmann constant k to estimate the diffusion co-efficient D of the analyte molecule to $D=10^{-6}$ cm$^2$s$^{-1}$ which we used for all further calculations and which corresponds to the literature (Metsämuronen et al., 2002) where comparable values for small molecules such as TNFα- are reported. The analyte viscosity was set to a high plasma viscosity (Koenig et al., 1998) of 2 mPa s.

The association and the dissociation from the capture site are described by the rate coefficients k, the analyte concentration C and the density of free binding sites ($\Theta_{max}-\Theta_t$) on the surface, using an ordinary differential equation of the form, $$\frac{d\Theta_t}{dt} = k_{on}C(\Theta_{max} - \Theta_t) - k_{off}\Theta_t$$

for monovalent receptors and ligands. $k_{on}$ is the rate constant for association, $k_{off}$ is the rate constant for dissociation, C is the concentration of free molecules in the fluid, $\Theta_t$ is the surface density at time t $\Theta_{max}$ is the maximum surface density of molecules calculated from the feature area of the individual capture molecules and is assumed to be constant over time. In this simulation we generally used $10^6 M^{-1}$ s$^{-1}$ for $k_{on}$ and $10^{-3}$ s$^{-1}$ for $k_{off}$ (Santora et al., 2001), but in some case these constants were modified." (Zimmermann, M. et al. "Modeling and Optimization of High Sensitivity, Low Volume Microfluidic-Based Surface Immunoassays." Biomedical Microdevices 7:2, 99-110, 2005, pp. 100-101)

In some embodiments, the equations from the Zimmermann passage can be used to determine a suitable assaying time that allows for satisfying assay sensitivity. For example, using a simulation incorporating the Zimmermann equations, and fitting in known or preferred parameter values, such as target analyte concentration, binding constant/coefficient between the target analyte and capture agent, surface density of immobilized capture agent in the assaying channel, numbers of analyte molecules to be captured during the assay to achieve the required assay sensitivity, one with ordinary skill in the art will be capable to work out a suitable assaying time based on the Zimmermann model.

A suitable assaying time can be also determined from empirical values. For example, to analyze protein composition in a whole blood sample, the assay time is usually about 1 hour. For an ELISA assay, each affinity binding step (e.g. primary antibody binding, secondary antibody binding) usually takes more than 10 minutes.

For a microfluidic chip of a certain design, the assaying time is dependent on the total volume of the assay fluid contained in the chambers and a flow rate through the assaying channel. The flow rate is dependent on the driving force of the absorbent material or pump and resistant force of channel that are experienced by the fluid. Accordingly, in some embodiments, after a suitable assaying time is determined, the design of the microfluidic chip, including volumes of the chambers, dimensions of the channels, and the type of absorbent material or pump which drives the flow of the fluid can be selected or modified accordingly so that a suitable assaying time and sensitivity is achieved. In addition, maintaining the flow rate above a minimum value stabilizes flow of fluid components of a sample and prevents precipitation of particles comprised in the sample onto the surfaces of the assaying channel, thus preventing the particles from interfering and/or damaging the capture agent barcode and the assay. For example, when analyzing whole blood samples, a minimum flow rate is estimated to be about 0.5 μL/min. According to an embodiment of the president disclosure, a serpentine mixing channel (112) reduces fluid concentration gradients within the cross section of the assaying channel (120). Dean vortices are generated in the curving parts or turns of the mixing channel (112) to induce transverse flow, while only simple Poiseuille flow occurs in straight channels of the microchip, pointing outwards in the same direction of the channel centerline. A fluidic path of the serpentine mixing channel (112) can further comprise irregular bumpers adapted to enhance chaotic mixing of the fluids while the fluids flow through. The serpentine mixing channel (112) ensures uniform distribution of fluid components in a cross-section of the channel that is perpendicular to the direction of fluid flow in the channel, thus ensures that the fluorescence intensity across the width of an assay barcode stripe in the assaying channel (120) is also uniform. This feature helps to reduce signal variation from the barcode, and increase the accuracy of the assay.

According to one embodiment of the present disclosure, the focusing channel (116) has a cross section of a high aspect ratio and focuses particles comprised in the fluid (such as blood cells in a whole blood sample) within a central region of the channels through hydrodynamic focusing without sheath flow. In a further embodiment, the focusing channel is about 10-20 μm in diameter or width, and more than about 0.5 mm long. The focusing channel is narrower than the following channels (e.g., the following assaying channel (120) is about 500 μm in diameter or width, according to one embodiment). The narrow channel structure of the focusing channel (116) creates inertial lift forces that axially focus the particles (e.g., blood cells) within the channel.

The inertial lift forces have multiple contributions that include the wall-repulsive force and the shear-lift force. The wall-repulsive force, for example, describes forces that are normal to a wall, and are experienced by a particle that is flowing parallel to that wall.

Wall-repulsive forces have not been recognized as important for particle alignment in small-scale microfluidic channels. However, when the channel size is reduced to a certain dimension, wall-repulsive forces become prominent.

Figure 2:
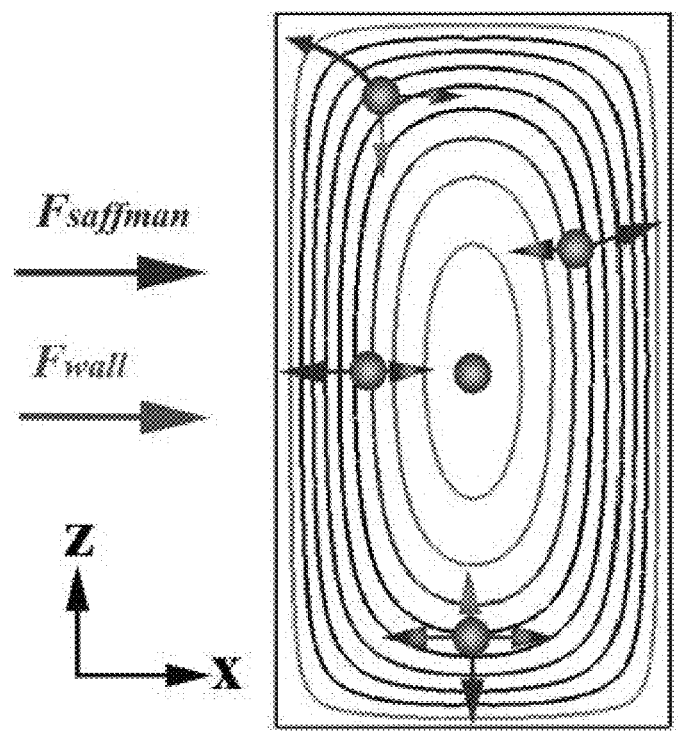
FIG. 2 depicts the forces a particle experiences in the focusing channel, according to one embodiment of the present disclosure.

When a particle (e.g., a blood cell) is flowing through the focusing channel (116), it experiences wall-repulsive forces in a direction normal to the wall, and towards the channel's center, due to stagnant flow close to the walls, as well as Saffman's lift force toward channel walls due to shear stress. FIG. 2 depicts the forces a particle experiences in the channel.

Figure 3:
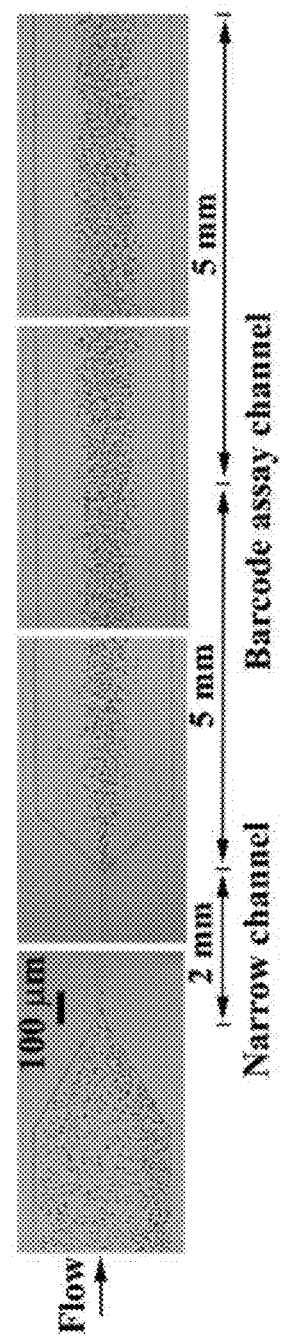
FIG. 3 depicts how the particles are focused when they pass the focusing channel, according to one embodiment of the present disclosure.

The interaction of those forces determines the transverse migration of the particle in the channel cross-section. According to one embodiment of the present disclosure, the magnitude of the wall-repulsive forces dominates all the other forces (including the Magnus force due to free rotation), resulting in particles migrating to the channel center and focusing into a single stream when exiting the narrow focusing channel (116) to the wide channel (118) and to the assaying channel (120), as shown in FIG. 3.

The focusing effect depends on several interacting factors, including the channel dimension, flow rate, size and shape of particles to be focused. Alteration in any of these factors may change the focusing effect.

In some embodiments, the cross-section perpendicular to the length of the focusing channel may be a rectangular, polygonal, elliptical or round. In other embodiments, the cross-section perpendicular to the length of the focusing channel can have irregular shapes.

In some embodiments, the cross-section perpendicular to the length of the focusing channel has a diameter or width of less than or equal to two times the diameter of the particles to be focused. In particular, the diameter or width of such cross-section can be from 1.5 to 2 times the diameter of particles.

In some embodiments, the cross-section perpendicular to the length of the focusing channel can have an aspect ratio of greater than about 1.5. In particular, the aspect ratio of such cross-section can be from about 1.5 to 2. In those embodiments wherein such cross-section has a rectangular shape, the aspect ratio can be calculated as the ratio between the length and width of the rectangle. In those embodiments wherein such cross-section has an elliptical shape, the aspect ratio can be calculated as the ratio between the major axis and minor axis of the ellipse.

Figure 4:
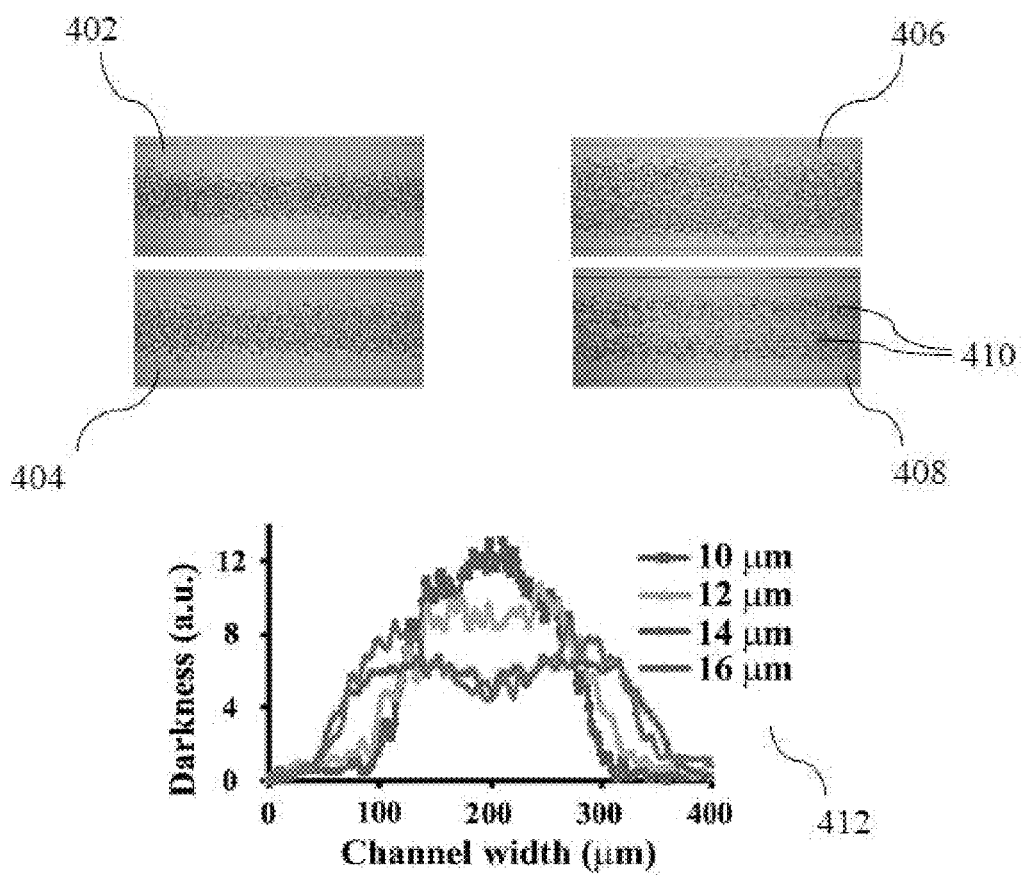
FIG. 4 depicts the focusing effects of focusing channel with different diameters, according to one embodiment of the present disclosure.

FIG. 4 shows the focusing effects of focusing channels with different diameters or width, according to one embodiment of the present disclosure. Section 402 depicts the focusing effects of a focusing channel 10 µm wide; section 404 shows the focusing effects of a focusing channel 12 µm wide; section 406 shows the focusing effects of a focusing channel 14 µm wide; Section 408 shows the focusing effects of a focusing channel 16 µm wide. As shown from FIG. 4, focusing occurs when the width of the focusing channel is less than ~12 p.m. Section 412 Plot showing how the diameter of the focusing channel influences the width of the fluid centroid that contains the blood cells. When the width is expanded to 16 µm, the particle stream (410) tends to be divided into two.

The fluid flow rate through the focusing channel can affect the focusing of particles. In particular, given a certain channel dimension, for particles within a certain size range, the flow rate has negligible effect on particle focusing. On the other hand, focusing effect of particles outside such size range is sensitive to the change of flow rate. For example, passing a whole blood sample through a channel of 10-15 µm in diameter, the focusing effect on blood cells of 6-9 µm in diameter is not significantly affected by the flow rate. However, focusing effect of particles of less than about 5 µm diameter in the sample is sensitive to the variation of flow rate.

Figure 5:
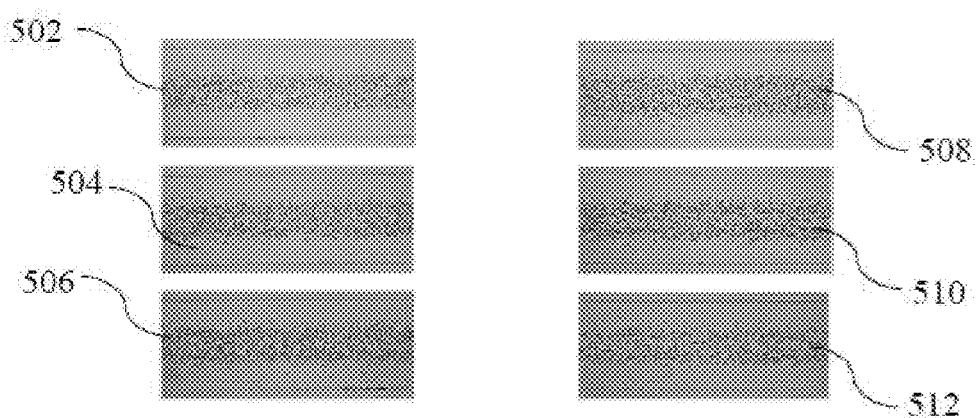
FIG. 5 depicts the focusing effects of a 12-μm diameter or width focusing channel at different flow rates, according to one embodiment of the present disclosure.

FIG. 5 shows the focusing effects of a 12-µm wide focusing channel at different flow rates (0.25 µL/min (502), 0.5 µL/min (504), 1 µL/min (506), 1.5 µL/min (508), 2 µL/min (510), and 4 µL/min (512)), according to one embodiment of the present disclosure. As can be seen from FIG. 5, in the range between 0.25 µL/min and 4 µL/min, the flow velocity has negligible effect on particle focusing.

Accordingly, given a certain channel dimension and flow rate, only particles of a specific size range are focused. For example, when flowing through a focusing channel of a diameter of about 15-20 µm at a rate of 1-5 µL/min, particles having about 10 µm diameter are focused at the center stream of the channel, whereas particles having about 0.5 diameters would not be focused, and thus distribute evenly in the channel.

According to one embodiment of the present disclosure, a filter paper can be inserted to the outlet (122) of FIG. 1. The capillarity of the filter paper, coupled with the hydrophilic nature of the fluidic channel surfaces, draws the fluid inside the channel toward the outlet (122). Accordingly, the flow rate depends on the strength of the wicking force and resistance force of the channels, and thus depends on the size and type of filter paper used and the dimensions of the channels. In a further embodiment, a filter paper (grade 50, Whatman) with thickness of 115 µm is selected. The filter paper with 1.5 $cm^2$ area can sustain wetting, and thus capillary-driven flow, for 2 hours.

According to other embodiments of the present disclosure, other mechanisms can be applied to drive the flow of fluid as alternatives to the absorbent material, such as a syringe pump, or a pneumatic pump.

According to one embodiment of the present disclosure, the fluids contained in the four chambers (102, 104, 106, 108) of FIG. 1 are drawn (drained) sequentially. That is, the fluid in chamber 108 is drawn to the channel before that in chamber 106; the fluid in chamber 106 is drawn before that in chamber 104, which is drawn before that in chamber 102. In other words, chamber 108 is drained first, chamber 106 next, then chamber 104, and chamber 102 last.

Figure 6:
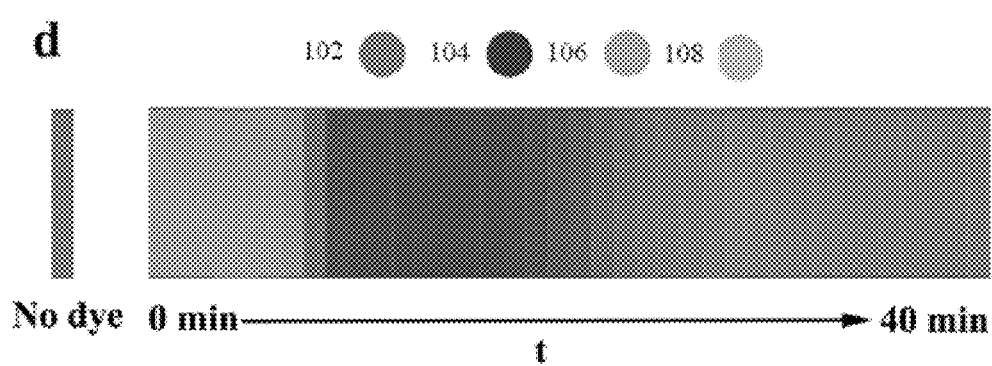
FIG. 6 depicts the real-time colorimetric imaging of a solution flowing through a section of the assaying channel, according to one embodiment of the present disclosure.

FIG. 6 shows the real-time colorimetric imaging of a solution flowing through a section of the barcode assaying channel, according to one embodiment of the present disclosure. In this embodiment, chambers 108, 106, 104, and 102 of FIG. 1 are loaded with 10, 8, 8, and 10 µL of dye solutions, respectively. The evolving shadings illustrate the time scale for the filter paper to sequentially drain the channels and complete the assay.

The dense posts inside the filter channels (110) of FIG. 1 can filter impurities. The posts also increase the flow resistances of the filter channels (110). This potentially retards mixing of fluids in one chamber with those from the neighboring chambers, and results in stepwise depletion. In addition, the capillarity in each chamber can also contribute to the stepwise depletion since typically as the fluid within a chamber is drained, the relative meniscus height increases.

In another embodiment, valves are added between chambers 102, 104, 106, and 108. The valves are so operated that fluids in the chambers are drained sequentially. Valves can be actuated magnetically, pneumatically, electrically, etc.

The sequential chamber depletion makes it possible to execute sequentially each of the steps for performing an assay in the assaying channel (120) without human intervention, such as performing the sequential steps of sample introduction, secondary antibody binding, fluorophore binding, and washing of a standard ELISA assay. FIG. 10 shows a table of the ssDNA oligomers used for the ELISA barcode assay, according to one embodiment of the present disclosure. The ssDNA oligomers are optimized to be orthogonal to one another, ensuring one species of DNA conjugated antibody only localizes to a specific stripe with minimal cross-reactivity. In a further embodiment, three strands of ssDNA are used to conjugate to one antibody and yields high DNA-antibody affinity to the ELISA barcode assay without compromising antibody activity. Sequence M is labeled with M'-Cy3 as a reference, and provides positional information for the remaining Cy5-labelled sequences on the barcode. More details of the method for assembling an antibody barcode using the DEL technology can be found in Ryan C. Bailey, et al. DNA-encoded Antibody Libraries: Unified Platform for Multiplexed Cell Sorting and Detection of Genes and Proteins. *Journal of the American Chemical Society,* 2007, 129 (7), pp 1959-1967, the disclosure of which is incorporated by reference in its entirety. By way of example and not of limitation, a procedure for producing DNA-antibody conjugates according to one embodiment of the present disclosure is provided below.

Prior to use, all antibodies were desalted, buffer exchanged to pH 7.4 PBS and concentrated to about 1 mg/mL using 3000 MWCO spin filters (Millipore). Succinimidyl 4-hydrazinonicotinate acetone hydrazone in N,N-dimethylformamide (DMF) (SANH, Solulink) was added to the antibodies at variable molar excess of (1000:1 to 5:1) of SANH to antibody. In this way the number of hydrazide groups introduced to the antibodies was varied. Separately, succinimidyl 4-formylbenzoate in DMF (SFB, Solulink) was added at a 20-fold molar excess to 5' aminated 26mer oligomers in PBS. This ratio of SFB to DNA ensured complete reaction of the 5' amine groups to yield 5' aldehydes. No further improvement in yield was observed for both the antibody and oligonucleotide coupling reactions after 4 h at room temperature. Excess SANH and SFB were removed and samples buffered exchanged to pH 6.0 citrate buffer using protein desalting spin columns (Pierce). A 20-fold excess of derivatized DNA was then combined with the antibody and allowed to react overnight at room temperature. Noncoupled DNA was removed with size exclusion spin columns (Bio-Gel P-30, Bio-Rad) or purified using a Pharmacia Superdex 200 gel filtration column at 0.5 mL/min isocratic flow of PBS. The synthesis of DNA-antibody conjugates was verified by non-reducing 7.5% Tris-HCl SDS-PAGE at relaxed denaturing conditions of 60° C. for 5 min and visualized with a molecular imager FX gel scanner (Bio-Rad). Conjugation reactions involving fluorescent antibodies or fluorescently labeled oligonucleotides were imaged similarly using appropriate excitation and emission filters.

Figure 12:
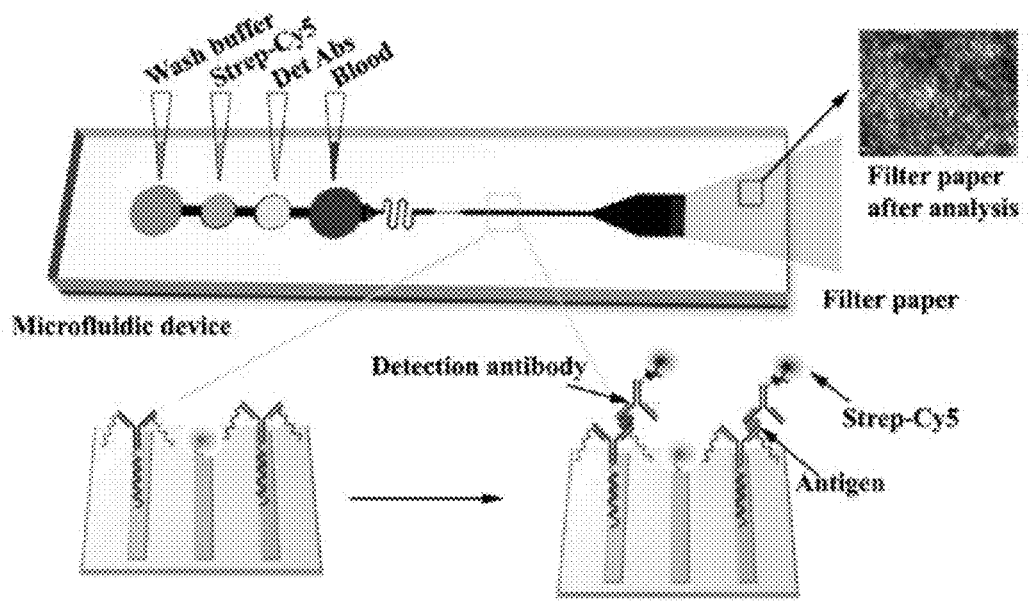
FIG. 12 illustrates the procedure for using the microchip, according to one embodiment of the present disclosure.

According to one embodiment of the present disclosure, the assaying channel (120) of FIG. 1 comprises capture agents suitable for binding a target material of the sample. Subsequently suitable reagents flow through the assaying channel (120) to detect the bound target material through an ELISA assay. The capture agents are fabricated in a barcode pattern on the surface of the assaying channel (120) through the process described above. A slice of filter paper (grade 50, Whatman) with the appropriate size is inserted into a slot that is connected to the outlet (122). 7 µL whole blood sample, 5 µL detection antibodies, 5 µL streptavidin-cy5 and 15 µL 3% BSA wt/v in PBS are loaded to chamber 108, 106, 104, and 102 respectively. Then, the filter paper is moved into the outlet (122) in contact with the fluid and draws the fluid toward the outlet. FIG. 12 illustrates the above procedure.

Because of the sequential chamber depletion, the whole blood sample in chamber 108 is drawn into the channel first. In a further embodiment, a small paper pre-filter is inserted into the base of the blood chamber (chamber 108), which removes 80-90% of the cells from the blood. This pre-purification, along with the posts inside the filter channel (110) keeps the channel from clogging.

The whole blood sample then passes through the mixing channel (112), and the focusing channel (116). Through the focusing channel, the blood cells are confined in the central region of the channel, and are kept a distance away from the channel walls. Thus, the blood cells are kept away from the surfaces of the capture agents when they reach the assaying channel (120). As a result, only plasma and plasma proteins contact the capture agents located on the wall of the assaying channel (120).

Subsequently, detection antibodies, streptavidin-cy5, and BSA in PBS are sequentially drawn through the assaying channel (120) for the remaining three steps of the ELISA assay: antibody binding, fluorophore binding, and washing.

In a further embodiment, the flow rate during the entire process is maintained at 0.5-1 µL/min. In a still further embodiment, the flow rate during the entire process is maintained between 0.67-1.34 mm/s.

Finally, the PDMS replica is peeled off the glass slide and a GenePix array scanner records the fluorescence levels from the individual barcode stripes of the assaying channel (120). Automated software routines convert those levels into protein abundances. Each barcode constitutes a complete copy of the panel of blood biomarker proteins assayed, and multiple barcodes are measured and averaged per pinprick assay.

According to one embodiment of the present disclosure, freshly collected pinpricks of blood are assayed for a panel of 11 proteins using the microfluidic chip and the procedure describe above. These proteins are c-terminal reactive protein (CRP), matrix metalloproteinase 3 (MMP3), serine proteinase inhibitor (Serpin), granulocyte colony-stimulating factor (GCSF), macrophage migration inhibitor factor (MIF), epidermal growth factor (EGF), chemokine (C-C motif) ligand 5 (CCL5), vascular endothelial growth factor (VEGF), interleukin 8 (IL-8), IL-1β, and interferon-gamma-induced protein (IP 10).

These proteins are variously associated with tumor progression, inflammation, and other disease conditions. One additional stripe is functionalized with mouse IgG1 isotype control to measure the level of non-specific binding for the assay. The ssDNA oligomers and antibodies for the protein panel are shown in FIG. 10 and FIG. 11, respectively.

Figure 13:
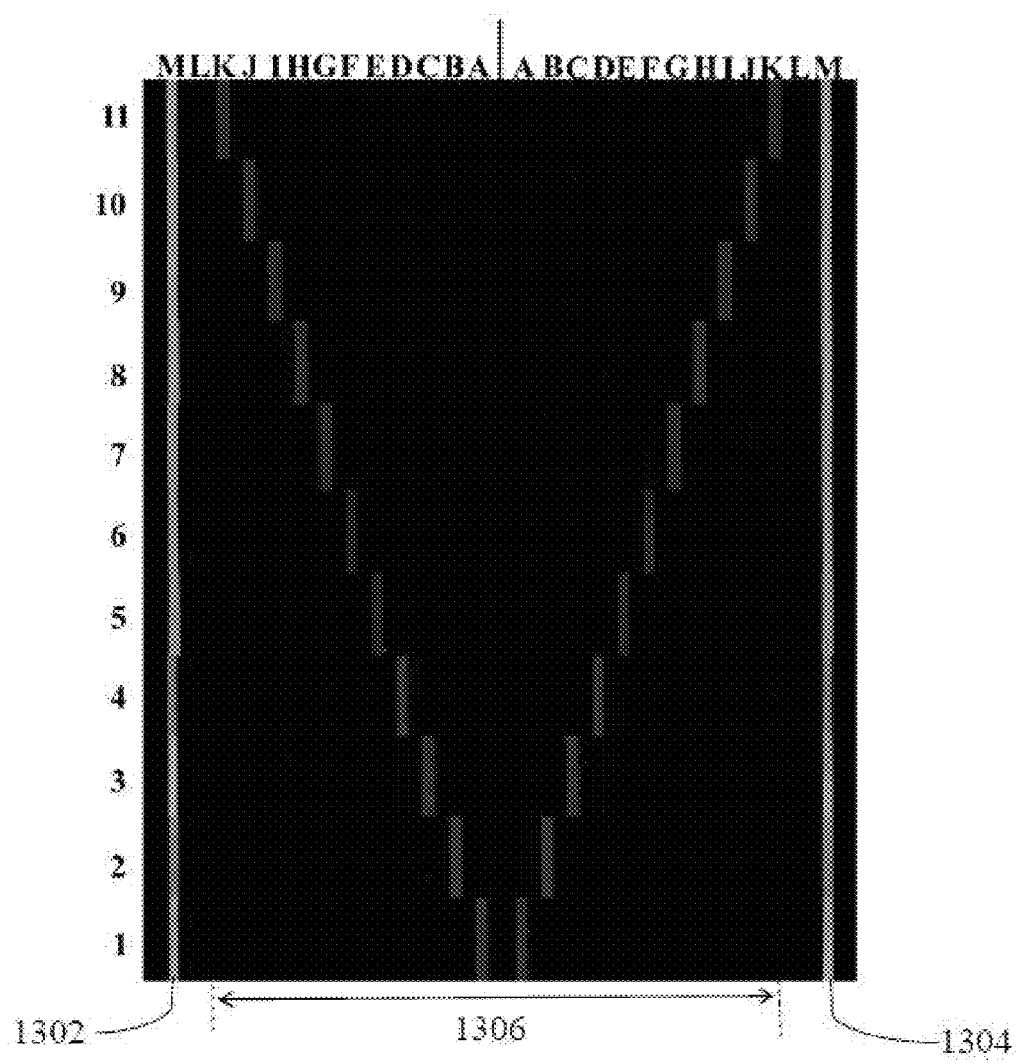
FIG. 13 depicts the cross-reactivity of a protein panel assay, according to one embodiment of the present disclosure.

FIG. 13 shows the cross-reactivity of the protein panel assay. Only one recombinant protein at 10 ng/ml was present in each sample to be detected (row). The red stripes (the stripes within the region 1306) indicate proteins detected. The green stripes (1302, 1304) are the references to spatially locate the red stripes and hence find the corresponding protein listed in FIG. 11.

Figure 14:
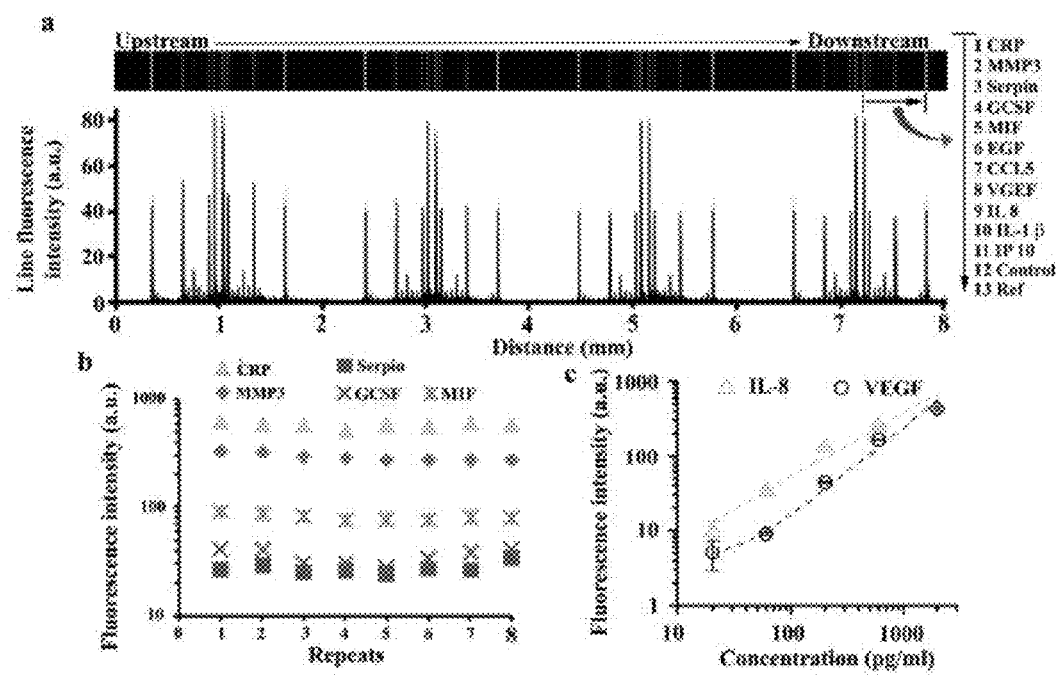
FIG. 14 depicts data collected from assaying a protein panel from a pinprick of whole blood using the microfluidic chip, according to one embodiment of the present disclosure.

FIG. 14 shows data collected from assaying a protein panel from a pinprick of whole blood using the microfluidic chip disclosed in the present disclosure. For this assay, a contact-activated lancet is used to prick a finger of a healthy donor. Immediately thereafter, a capillary blood collection tube pre-filled with 1 µL of 150 mM citrate anticoagulant solution is used to collect ~10 µL blood, which is then transferred to chamber 108 of the microfluidic chip of FIG. 1 with chambers 102, 104 and 106 already pre-filled with their designated reagents. Two duplicate microfluidic chips are prepared for triplicate measurements to test the reproducibility of the barcode assays. Filter paper is then inserted at the end of each device, and after 40 minutes the assays are complete. The PMDS replica is peeled off each glass slide, and the barcode fluorescence intensities is scanned and digitized using a Genepix array scanner and custom written software. FIG. 14*a* shows the fluorescence data for the eight-barcode-group assays, both in image and digitized form, from one of these three chips. These assays, along with the statistical analysis of FIG. 14*b*, illustrate how highly uniform barcoding chemistry translates into highly reproducible protein assays.

Four of the proteins in the panel, including VEGF (detection limit ~60 pg/ml (1.3 pM)) and IL-8 (detection limit ~20 pg/ml (2.5 pM)), are found below the detection threshold, which is not surprising for a healthy donor. The detection limits for these assays are slightly higher than the manufacturer specifications for the individual ELISA assays (~15 pg/ml for IL8 and ~30 pg/ml for VEGF, as shown in FIG. 14c).

According to one embodiment of the present disclosure, at sufficiently high flow velocity, the time to complete a flow-through assay is limited by the kinetics of antibody/analyte binding, rather than by diffusion (as in a standard 96-well plate format). In a further embodiment, the flow velocity of blood through the assaying channel is ~1 mm/sec, which implies that the assay should be nearly kinetically limited, with each assay step requiring ~5-10 minutes.

Figure 15:
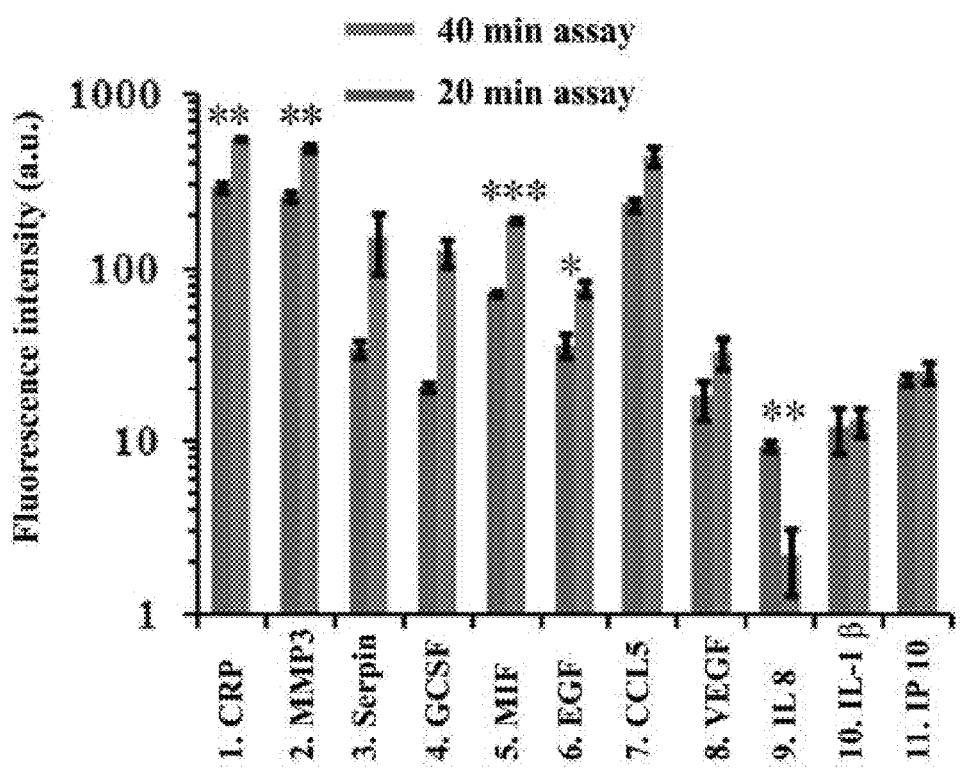
FIG. 15 depicts the assay data for the microfluidic chips with two different assay time: 20 minutes and 40 minutes, according to one embodiment of the present disclosure.

Therefore, the assay time can be changed by varying the amount of fluids loaded in chambers 102, 104, 106, and 108 of FIG. 1. FIG. 15 shows the assay data for the microfluidic chips with two different assay time: 20 minutes and 40 minutes (corresponding to 5 and 10 minutes per step). The amount of protein detected in the 40-minute assay is slightly higher than that in the 20-minute assay.

Figure 16:
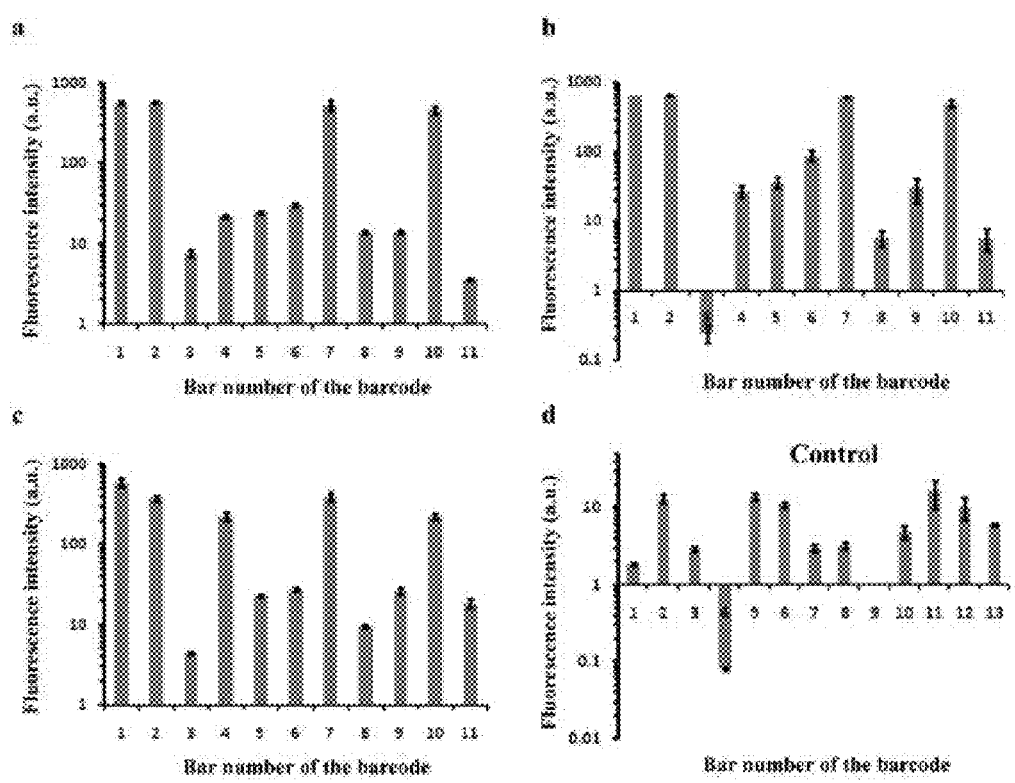
FIG. 16 depicts quantified results of 3 blood samples from different donors and a control sample analyzed by 40-minute assays, according to one embodiment of the present disclosure.

FIG. 16 shows quantified results of 3 blood samples from different donors analyzed by 40-minute assays (FIGS. 16a, 16b, and 16c). For each stripe, the eight repeated barcode groups are averaged and the standard deviations are generated to present error bars. FIG. 16d shows the control values obtained by performing the same procedure as FIGS. 16a-16c, except that the DNA-encoded capture antibodies are not patterned in the microchip, and so only background binding to the DNA oligomers is observed. Note that the y-axis of this plot is significantly enlarged compared to those for the blood samples.

According to a second aspect of the present disclosure, a method for separating a fluid into a first component and a second component is described. The first component of the fluid comprises particles within a certain size range. The method comprises providing a channel, the channel having a dimension which is a function of the size range of the particles and delivering the fluid through the channel at a set flow rate.

In some embodiments, a cross-section of the channel has a diameter or width which is less than or equal to about 2 times the diameter of the particles. In particular, in some embodiments, a cross-section of the channel has a diameter or width which is from about 1.5 to about 2 times the diameter of the particles.

In some embodiments, the channel has a cross-section of an aspect ratio of more than or equal to about 1.5. In particular, in some embodiments, the channel has a cross-section of an aspect ratio of from about 1.5 to about 2.

In some embodiments, the method can be used to separate blood cells from other components of a whole blood sample. The method further comprises diluting the whole blood sample, such as 2-3 times, before the delivering.

The examples set forth above are provided to give those of ordinary skill in the art a complete disclosure and description of how to make and use the embodiments of the arrangements, devices, and methods of the disclosure, and are not intended to limit the scope of what the inventors regard as their disclosure. All patents and publications mentioned in the specification are indicative of the levels of skill of those skilled in the art to which the disclosure pertains.

The entire disclosure of each document cited (including patents, patent applications, journal articles, abstracts, laboratory manuals, books, or other disclosures) in the Background, Summary, Detailed Description, and Examples is hereby incorporated herein by reference. All references cited in this disclosure are incorporated by reference to the same extent as if each reference had been incorporated by reference in its entirety individually. However, if any inconsistency arises between a cited reference and the present disclosure, the present disclosure takes precedence.

Further, the hard copy of the sequence listing submitted herewith and the corresponding computer readable form are both incorporated herein by reference in their entireties.

The terms and expressions which have been employed herein are used as terms of description and not of limitation, and there is no intention in the use of such terms and expressions of excluding any equivalents of the features shown and described or portions thereof, but it is recognized that various modifications are possible within the scope of the disclosure claimed Thus, it should be understood that although the disclosure has been specifically disclosed by preferred embodiments, exemplary embodiments and optional features, modification and variation of the concepts herein disclosed can be resorted to by those skilled in the art, and that such modifications and variations are considered to be within the scope of this disclosure as defined by the appended claims.

It is also to be understood that the terminology used herein is for the purpose of describing particular embodiments only, and is not intended to be limiting. As used in this specification and the appended claims, the singular forms "a," "an," and "the" include plural referents unless the content clearly dictates otherwise. The term "plurality" includes two or more referents unless the content clearly dictates otherwise. Unless defined otherwise, all technical and scientific terms used herein have the same meaning as commonly understood by one of ordinary skill in the art to which the disclosure pertains.

When a Markush group or other grouping is used herein, all individual members of the group and all combinations and possible subcombinations of the group are intended to be individually included in the disclosure. Every combination of components or materials described or exemplified herein can be used to practice the disclosure, unless otherwise stated. One of ordinary skill in the art will appreciate that methods, device elements, and materials other than those specifically exemplified can be employed in the practice of the disclosure without resort to undue experimentation. All art-known functional equivalents, of any such methods, device elements, and materials are intended to be included in this disclosure. Whenever a range is given in the specification, for example, a temperature range, a frequency range, a time range, or a composition range, all intermediate ranges and all subranges, as well as, all individual values included in the ranges given are intended to be included in the disclosure. Any one or more individual members of a range or group disclosed herein can be excluded from a claim of this disclosure. The disclosure illustratively described herein suitably can be practiced in the absence of any element or elements, limitation or limitations which is not specifically disclosed herein.

A number of embodiments of the disclosure have been described. The specific embodiments provided herein are examples of useful embodiments of the disclosure and it will be apparent to one skilled in the art that the disclosure can be carried out using a large number of variations of the devices, device components, methods steps set forth in the present description. As will be obvious to one of skill in the art, methods and devices useful for the present methods can include a large number of optional composition and processing elements and steps.

In particular, it will be understood that various modifications may be made without departing from the spirit and scope of the present disclosure. Accordingly, other embodiments are within the scope of the following claims.

LIST OF REFERENCES

1. N. L. Anderson and N. G. Anderson, *Mol. Cell. Proteomics*, 2002, 1, 845-867.
2. S. Ray, M. Britschgi, C. Herbert, Y. Takeda-Uchimura, A. Boxer, K. Blennow, L. F. Friedman, D. R. Galasko, M. Jutel, A. Karydas, J. A. Kaye, J. Leszek, B. L. Miller, L. Minthon, J. F. Quinn, G. D. Rabinovici, W. H. Robinson, M. N. Sabbagh, Y. T. So, D. L. Sparks, M. Tabaton, J. Tinklenberg, J. A. Yesavage, R. Tibshirani and T. Wyss-Coray, *Nat. Med.*, 2007, 13, 1359-1362.
3. A. A. Kamat, M. Baldwin, D. Urbauer, D. Dang, L. Y. Han, A. Godwin, B. Y. Karlan, J. L. Simpson, D. M. Gershenson, R. L. Coleman, F. Z. Bischoff and A. K. Sood, *Cancer-Am. Cancer Soc.*, 2010, 116, 1918-1925.
4. R. Fan, O. Vermesh, A. Srivastava, B. K. H. Yen, L. D. Qin, H. Ahmad, G. A. Kwong, C. C. Liu, J. Gould, L. Hood and J. R. Heath, *Nat. Biotechnol.*, 2008, 26, 1373-1378.
5. L. Gervais and E. Delamarche, *Lab Chip*, 2009, 9, 3330-3337.
6. A. W. Martinez, S. T. Phillips, M. J. Butte and G. M. Whitesides, *Angew. Chem. Int. Edit.*, 2007, 46, 1318-1320.
7. G. A. Posthuma-Trumpie, J. Korf and A. van Amerongen, *Anal. Bioanal. Chem.*, 2009, 393, 569-582.
8. L. D. Qin, O. Vermesh, Q. H. Shi and J. R. Heath, *Lab Chip*, 2009, 9, 2016-2020.
9. Y. S. Shin, H. Ahmad, H. J. Kim, Q. H. Shi, T. A. Charles-Pascal, R. Fan, I. Goddard, W. A. and J. R. Heath, *ChemPhyChem*, 2010, 11, 3063-3069.
10. G. F. Zheng, F. Patolsky, Y. Cui, W. U. Wang and C. M. Lieber, *Nat. Biotechnol.*, 2005, 23, 1294-1301.
11. R. C. Bailey, G. A. Kwong, C. G. Radu, O. N. Witte and J. R. Heath, *J. Am. Chem. Soc.*, 2007, 129, 1959-1967.
12. C. Boozer, J. Ladd, S. F. Chen and S. T. Jiang, *Anal. Chem.*, 2006, 78, 1515-1519.
13. C. M. Niemeyer, *Nano Today*, 2007, 2, 42-52.
14. P. Cherukat and J. B. Mclaughlin, *J. Fluid Mech.*, 1994, 263, 1-18.
15. M. Yamada, M. Nakashima and M. Seki, *Anal. Chem.*, 2004, 76, 5465-5471.
16. S. C. Hur, H. T. K. Tse and D. Di Carlo, *Lab Chip*, 2010, 10, 274-280.
17. J. Wang, Y. H. Zhan, V. M. Ugaz and C. Lu, *Lab Chip*, 2010, 10, 2057-2061.
18. K. Svanes and B. W. Zweifach, *Microvas. Res.*, 1968, 1, 210-220.
19. Y. C. Fung, *Microvas. Res.*, 1973, 5, 34-48.
20. S. Yang, A. Undar and J. D. Zahn, *Lab Chip*, 2006, 6, 871-880.
21. C. F. Nathan, T. J. Prendergast, M. E. Wiebe, E. R. Stanley, E. Platzer, H. G. Remold, K. Welte, B. Y. Rubin and H. W. Murray, *J. Exp. Med.*, 1984, 160, 600-605.
22. A. D. Luster, *New Engl. J. Med.*, 1998, 338, 436-445.
23. B. Kaur, F. W. Khwaja, E. A. Severson, S. L. Matheny, D. J. Brat and E. G. Van Meir, *Neuro. Oncol.*, 2005, 7, 134-153.
24. Y. S. Hamirani, S. Pandey, J. J. Rivera, C. Ndumele, M. J. Budoff, R. S. Blumenthal and K. Nasir, *Atherosclerosis*, 2008, 201, 1-7.
25. M. Zimmermann, E. Delamarche, M. Wolf and P. Hunziker, *Biomed. Microdevices*, 2005, 7, 99-110.
26. J. Wang, N. Bao, L. L. Paris, H. Y. Wang, R. L. Geahlen and C. Lu, *Anal. Chem.*, 2008, 80, 1087-1093.
27. S. H. Kim, Y. Yang, M. Kim, S. W. Nam, K. M. Lee, N. Y. Lee, Y. S. Kim and S. Park, *Adv. Funct. Mater.*, 2007, 17, 3493-3498.
28. E. P. Dupont, R. Luisier and M. A. M. Gijs, *Microelectron. Eng.*, 2010, 87, 1253-1255.
29. A. P. Sudarsan and V. M. Ugaz, *Proc. Natl. Acad. Sci. USA*, 2006, 103, 7228-7233.
30. S. H. Kim, Y. Yang, M. Kim, S. W. Nam, K. M. Lee, N. Y. Lee, Y. S. Kim and S. Park, *Adv. Funct. Mater.*, 2007, 17, 3493-3498.
31. E. P. Dupont, R. Luisier and M. A. M. Gijs, *Microelectron. Eng.*, 2010, 87, 1253-1255.
32. D. Di Carlo, D. Irimia, R. G. Tompkins and M. Toner, *Proc. Natl. Acad. Sci. USA*, 2007, 104, 18892-18897.
33. J. F. Edd, D. Di Carlo, K. J. Humphry, S. Koster, D. Irimia, D. A. Weitz and M. Toner, *Lab Chip*, 2008, 8, 1262-1264.
34. R. C. Bailey, G. A. Kwong, C. G. Radu, O. N. Witte and J. R. Heath, *J. Am. Chem. Soc.*, 2007, 129, 1959-1967.

The invention claimed is:

1. A microfluidic device for controlling flow of a first fluid component and a second fluid component in a fluid sample, the first fluid component comprising at least one target, the device comprising:
   an inlet channel for introducing the fluid sample in the microfluidic device;
   a focusing channel in fluidic communication with the inlet channel; and
   an assaying channel in fluidic communication with the focusing channel, the assaying channel carrying at least one capture agent or component thereof, the at least one capture agent or component thereof attached to the assaying channel, the at least one capture agent having a binding affinity for the target,
   wherein
      the focusing channel is adapted to move the second fluidic component of the fluid sample in a distance away from surfaces of the assaying channel and keep the first fluid component in contact with the at least one capture agent or component thereof; and
   a sequential loading device in fluidic communication with the inlet channel, the sequential loading device comprising:
      an outlet channel in fluidic communication with the inlet channel;
      a first loading chamber in fluidic communication with the outlet channel;
      a second loading chamber in fluidic communication with the outlet channel; and
      a sequential flow control in fluidic communication with the second loading chamber,
      wherein
         the sequential flow control is adapted to impede the fluid of the second loading chamber to flow into the outlet channel before the fluid in the first chamber is depleted through the outlet.

2. The microfluidic device of claim 1, further comprising an absorbent material in contact with fluid at the end of the assaying channel, wherein
   the absorbent material is configured to draw the fluid from the inlet toward the assaying channel.

3. The microfluidic device of claim 2, wherein the absorbent material is a filter paper adapted to draw the fluid via capillary action.

4. The microfluidic device of claim 1, wherein the assaying channel comprises a DNA configured in a barcode pattern.

5. The microfluidic device of claim 1, wherein the assaying channel comprises an antibody configured in a barcode pattern.

6. The microfluidic device of claim 5, wherein the antibody barcode pattern is configured for an ELISA assay.

7. The microfluidic device of claim 1, wherein
   the fluidic sample comprises blood;
   the first fluid component comprises plasma; and
   the second fluid component comprises blood cells.

8. The microfluidic device of claim 1, wherein the focusing channel comprises a channel narrower than the assaying channel.

9. The microfluidic device of claim 1, wherein the focusing channel comprises a channel that has a diameter or width less than or equal to two times the diameter of the second fluid component.

10. The microfluidic device of claim 1, wherein the focusing channel comprises a channel that is 10-20 microns in diameter or width.

11. The microfluidic device of claim 1, wherein the focusing channel comprises a channel that has an aspect ratio greater than 1.5.

12. The microfluidic device of claim 1, further comprising a mixing channel in fluidic communication with, and located between, the inlet channel and the focusing channel, wherein the mixing channel is adapted to mix fluid flowing through the mixing channel.

13. The microfluidic device of claim 12, wherein the mixing channel is adapted to generate Dean Vortices inside the mixing channel.

14. The microfluidic device of claim 1, wherein the sequential flow control comprises a magnetic valve.

15. A microfluidic device for controlling flow of a first fluid component and a second fluid component in a fluid sample, the first fluid component comprising at least one target, the device comprising:

an inlet channel for introducing the fluid sample in the microfluidic device;

a focusing channel in fluidic communication with the inlet channel;

an assaying channel in fluidic communication with the focusing channel, the assaying channel carrying at least one capture agent or component thereof, the at least one capture agent or component thereof attached to the assaying channel, the at least one capture agent having a binding affinity for the target, wherein the focusing channel is adapted to move the second fluidic component of the fluid sample in a distance away from surfaces of the assaying channel and keep the first fluid component in contact with the at least one capture agent or component thereof; and a sequential loading device in fluidic communication with the inlet channel, the sequential loading device comprising:

an outlet channel in fluidic communication with the inlet channel;

a first loading chamber in fluidic communication with the outlet channel;

a second loading chamber in fluidic communication with the outlet channel; and a sequential flow control in fluidic communication with the second loading chamber, wherein the sequential flow control is adapted to impede the fluid of the second loading chamber to flow into the outlet channel before the fluid in the first chamber is depleted through the outlet and wherein the sequential flow control comprises a channel having posts inside.

16. The microfluidic device of claim 15, further comprising a mixing channel in fluidic communication with, and located between, the inlet channel and the focusing channel, wherein the mixing channel is adapted to mix fluid flowing through the mixing channel, wherein the sequential flow control comprises a filter channels connecting the first chamber, with the second chamber and the first chamber with the mixing channel, and wherein the a filter channel connecting the first loading chamber and the mixing chamber, has a majority of the posts relative to the filter channels of the sequential flow control.

17. A method for separating a fluid into a first fluid component and a second fluid component, the second fluid component comprising particles within a certain size range, the method comprising:

providing a channel, the channel having a dimension which is a function of the size range of the particles; and delivering the fluid through the channel at a set flow rate within the microfluidic device according to claim 1.

18. The method according to claim 17, wherein a cross-section of the channel has a diameter or width which is less than or equal to about 2 times the diameter of the particles.

19. The method according to claim 18, wherein a cross-section of the channel has a diameter or width which is about 1.5 to about 2 times the diameter of the particles.

20. The method according to claim 17, wherein the channel has a cross-section of an aspect ratio of equal to or more than about 1.5.

21. The method according to claim 20, wherein the channel has a cross-section of an aspect ratio of about 1.5 to about 2.

22. The method according to claim 17, wherein when the fluid is a whole blood sample, the method further comprises diluting the whole blood sample before the delivering.

\* \* \* \* \*